(12) United States Patent
Yamakawa et al.

(10) Patent No.: US 10,539,516 B2
(45) Date of Patent: *Jan. 21, 2020

(54) X-RAY INSPECTION APPARATUS AND X-RAY INSPECTION METHOD

(71) Applicant: JOB CORPORATION, Kanagawa (JP)

(72) Inventors: Tsutomu Yamakawa, Kanagawa (JP); Shuichiro Yamamoto, Kanagawa (JP); Masashi Yamasaki, Kanagawa (JP)

(73) Assignee: JOB CORPORATION, Kanagawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/007,018

(22) Filed: Jun. 13, 2018

(65) Prior Publication Data

US 2018/0292332 A1 Oct. 11, 2018

Related U.S. Application Data

(63) Continuation of application No. 14/900,251, filed as application No. PCT/JP2015/051911 on Jan. 23, 2015, now Pat. No. 10,024,807.

(30) Foreign Application Priority Data

Jan. 23, 2014 (JP) .................................. 2014-010709

(51) Int. Cl.
*G01N 23/00* (2006.01)
*G01N 23/046* (2018.01)
(Continued)

(52) U.S. Cl.
CPC .............. *G01N 23/046* (2013.01); *A61B 6/02* (2013.01); *A61B 6/14* (2013.01); *A61B 6/12* (2013.01);
(Continued)

(58) Field of Classification Search
CPC ... A61B 5/0059; A61B 5/7257; A61B 5/7264; A61B 5/7267; A61B 6/032; A61B 6/02;
(Continued)

(56) References Cited

U.S. PATENT DOCUMENTS 6,028,910 A 2/2000 Kirchner
6,850,589 B2 * 2/2005 Heumann ............ G01N 23/046
378/19

(Continued)

FOREIGN PATENT DOCUMENTS

JP 2007-524438 8/2007
WO 2005/083403 9/2005
(Continued)

*Primary Examiner* — Irakli Kiknadze
(74) *Attorney, Agent, or Firm* — Clark & Brody

(57) ABSTRACT

Frame data of tomographic planes that are parallel in the scan direction and between an X-ray tube and an X-ray detecting unit is generated based on detected frame data. The generation of frame data is based on the fan-shaped spreading of an X-ray beam and the differences in position in a height direction between the tomographic planes from a detection surface. Tomographic images are respectively generated from the frame data of the tomographic planes based on laminography technique. Edge information based on the changes in pixel values in each tomographic image is calculated for each pixel. A three-dimensional distribution of the edge information is generated and the edge information is searched in a direction passing through the tomographic planes and pixels indicating a maximum value in the edge information are detected. Only pixels in the tomographic images that positionally correspond to detected pixels are combined into a single composite image.

15 Claims, 22 Drawing Sheets

(51) Int. Cl.
*A61B 6/02* (2006.01)
*A61B 6/14* (2006.01)
*A61B 6/12* (2006.01)

(52) U.S. Cl.
CPC . *G01N 2223/401* (2013.01); *G01N 2223/619* (2013.01); *G01N 2223/643* (2013.01)

(58) Field of Classification Search
CPC ........... A61B 6/06; A61B 6/583; A61B 6/585; A61B 5/725; A61B 5/7203; A61B 6/00; A61B 6/037; A61B 6/12; A61B 6/14; A61B 6/027; A61B 6/4085; G01N 2223/401; G01N 2223/619; G01N 2223/643; G01N 23/044; G01N 23/046; G01N 2223/419; G01N 23/04; A61K 31/716; A61K 31/717; A61K 9/0056; A61K 9/2009; A61K 9/2054; A61K 9/2059; A61K 9/2077; G21K 1/025; G06T 2207/10072; G06T 2207/10088; G06T 2207/30048; G06T 7/0012; G06T 7/11; G06T 7/174; G06T 7/62; G06T 2207/20141; G06T 2207/20148; G06T 7/0081; G06T 7/0095; G06T 7/0097; G06T 7/602
USPC .................................................. 378/4, 19, 62
See application file for complete search history.

(56) References Cited

U.S. PATENT DOCUMENTS

| | | | |
|---|---|---|---|
| 7,016,458 B2* | 3/2006 | Francke | A61B 6/032 378/19 |
| 7,729,468 B2* | 6/2010 | Shimono | G01N 23/046 378/10 |
| 2004/0252811 A1 | 12/2004 | Morita et al. | |
| 2005/0008124 A1 | 1/2005 | Ullberg | |
| 2006/0023959 A1 | 2/2006 | Yang et al. | |
| 2006/0203959 A1 | 9/2006 | Spartiotis | |
| 2008/0292169 A1* | 11/2008 | Wang | G06T 7/0012 382/131 |
| 2009/0310845 A1 | 12/2009 | Ogawa et al. | |
| 2010/0034340 A1 | 2/2010 | Spartiotis | |
| 2011/0019797 A1 | 1/2011 | Morton | |
| 2011/0182401 A1 | 7/2011 | Anashkin | |
| 2012/0230467 A1 | 9/2012 | Katsumata et al. | |
| 2012/0328071 A1* | 12/2012 | Katsumata | A61B 6/14 378/4 |

FOREIGN PATENT DOCUMENTS

| | | |
|---|---|---|
| WO | 2011/016508 | 2/2011 |
| WO | 2012/086648 | 6/2012 |

* cited by examiner

FIG.20
[RECONSTRUCTION OF IMAGES IN CASE OF A PLURALITY OF DETECTORS ARRANGED PARALLEL TO EACH OTHER]
(A)
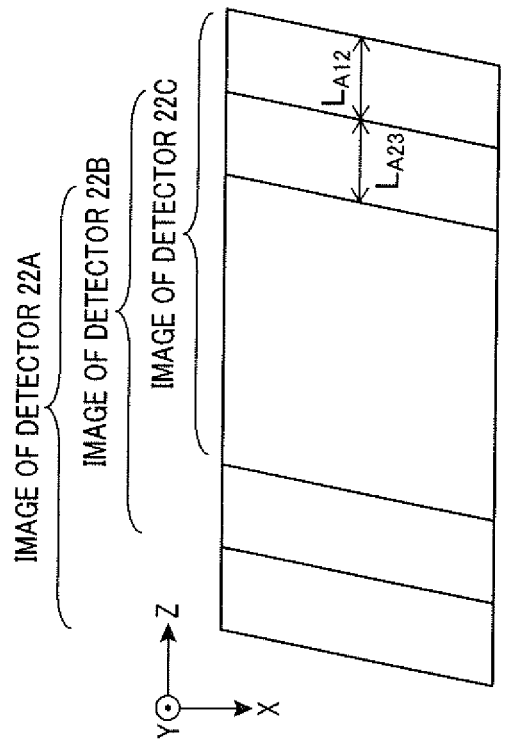
(B)
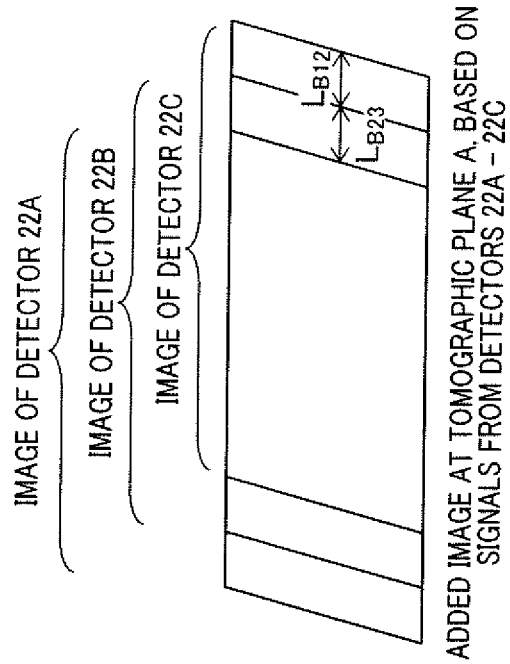

FIG.22
(A)
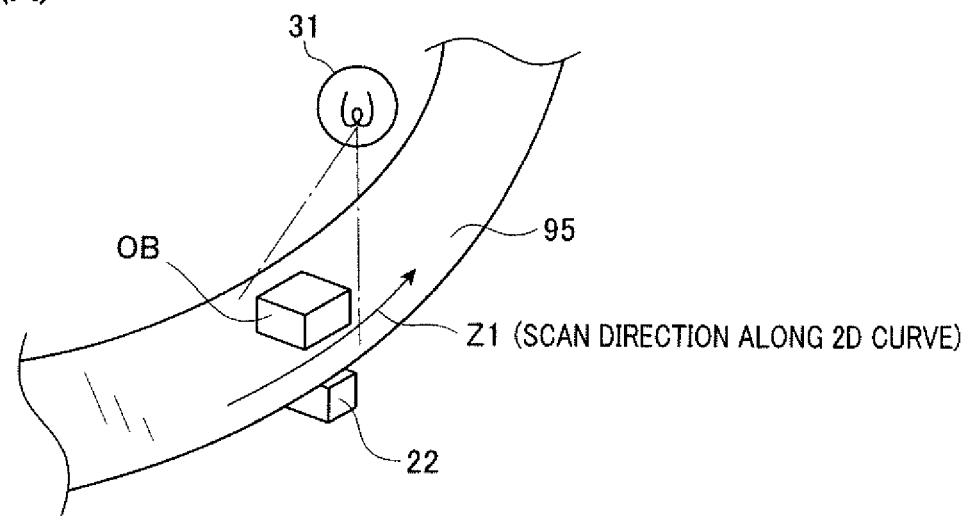
(B)
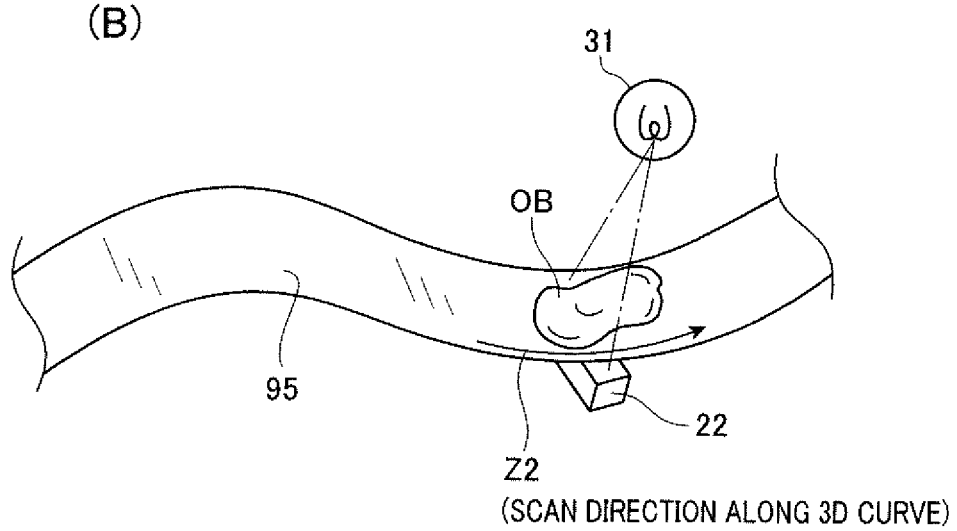

X-RAY INSPECTION APPARATUS AND X-RAY INSPECTION METHOD

CROSS-REFERENCE TO RELATED APPLICATION

This application is a Continuation of U.S. Ser. No. 14/900,251 filed on Dec. 21, 2015, which is a national phase of PCT/JP2015/051911 filed on Jan. 23, 2015, which claims benefit of priority from earlier Japanese Patent Application No. 2014-010709 filed Jan. 23, 2014 the description of which are incorporated herein by reference.

TECHNICAL FIELD

The present invention relates to an X-ray inspection apparatus and an X-ray inspection method in which X-rays are used to inspect the inside of an object. In particular, the present invention relates to an X-ray inspection apparatus and an X-ray inspection method that is, for example, suitable for inspecting the presence of foreign matter that may be present inside or on the outer surface of an object, such a food product, a manufactured product, or a part of a human body, such as a breast, as well as for inspecting the presence of an object of interest. The foreign matter is a substance that has a composition differing from that of the object.

BACKGROUND ART

In recent years, from the perspective of public health and food safety, there has been an increasing need for inspection of foreign matter that may be contained inside food products.

While the methods of X-ray inspection are numerous, an inspection method that is receiving attention is a method in which X-rays are used to collect information on a substance inside a food product. As an example for achieving the foregoing, a so-called in-line-type X-ray inspection apparatus is known. In the in-line-type X-ray inspection apparatus, an X-ray tube and a detector are arranged above and below a conveyor belt that is sandwiched therebetween. The in-line-type X-ray inspection apparatus uses X-rays to inspect a food product to be inspected that is placed on the belt. In the case of this apparatus, the food product to be inspected is placed on the belt (line) and conveyed such as to pass through an X-ray radiation field of the X-ray tube. The X-rays that are transmitted through the passing food product are detected by the detector on the underside of the belt. An image is then generated based on the detection data. As a result of image processing being performed on the generated image by software, the presence and the type of foreign matter that may have become mixed into the food product can be discovered. In addition, the target of inspection is not limited to foreign matter. The inspection may target an object in which a difference in contrast occurs through X-rays, and of which the size, shape, or weight is required to be more accurately determined.

Therefore, this in-line-type X-ray inspection apparatus is suitable for instances in which a large number of food products are to be inspected on an assembly line. A specific example of this X-ray apparatus is as follows. Food products to be inspected (for example, vegetables such as green peppers, food items such as manufactured bread, or blocks of meat) are placed on a conveyor belt that, for example, advances 60 m per minute. An X-ray generator is set above the belt. In addition, a vertically long X-ray detector is set on the underside of the belt on which the food products are placed, or in other words, in the center of a circulating belt. The X-ray detector has a detection surface that covers the overall width of the line. The detector outputs frame data at a fixed rate. The pieces of frame data are mutually added, for example, synchronously with the movement speed of the conveyor belt.

At present, a detector in which a scintillator and a photoelectric conversion element are combined is often used. A reason for this is to enhance X-ray detection sensitivity to X-ray energy in the range of about 20 keV to 150 keV. A scintillator such as cesium iodine (CsI) or gadolinium oxysulfide (GOS) is typically used as the scintillator. Therefore, the scintillator has a relatively low response speed, has decay characteristics, and has a relatively narrow dynamic range. Consequently, restrictions are applied to apparatus operation on the user side. For example, the object to be inspected is restricted to food products that are thin in thickness and have relatively low X-ray absorption, and the amount of food products fed onto the line is suppressed.

A food product inspection apparatus (foreign matter detection apparatus) that uses a dual-energy detector to even slightly reduce such restrictions is also known. In the food product inspection apparatus, a detector that absorbs low-energy X-rays and a detector that absorbs high-energy X-rays are arranged in an overlapping manner. In the case of this apparatus, a scheme is implemented in which two types of images are separately reconfigured based on the respective frame data outputted from the two detectors. Foreign matter is then visualized through calculation of the difference between the two images. However, resolution is insufficient even in this apparatus. To meet needs, such as the need to check for even small pieces of foreign matter measuring about 0.3 mm, for example, restrictions, such as reducing speed, restricting objects to be inspected to thin objects, and arranging the objects to be inspected in a more dispersed manner, are applied. Stable inspection of the differences in X-ray absorption regarding such small pieces of foreign matter is difficult.

Realistically, when an image of a single tomographic plane (or cross-section) in a height direction on the belt is viewed, detection of foreign matter that is present on the tomographic plane or in a position near the tomographic plane is possible. However, detection of foreign matter that is present away from the tomographic plane or in a three-dimensional manner is difficult.

In consideration of such perspectives, a method and an apparatus for generating images of multiple tomographic planes, described in JP-A-2012-509735, which is described in PTL 1, are also known. The invention described in this publication gives an example in which a photon-counting X-ray detector is combined with a tomosynthesis technique. Images of a plurality of slice planes of a subject are obtained for use in mammography, based on frame data of a desired X-ray energy bin. This tomosynthesis technique is also referred to as a laminography technique in the field of non-destructive inspection.

A similar method for imaging multiple tomographic planes is also described in JP-A-2005-13736, which is described in PTL 2.

CITATION LIST

Patent Literature

[PTL 1] JP-A-2012-509735
[PTL 2] JP-A-2005-13736

SUMMARY OF INVENTION

Technical Problem

However, the above-described imaging methods described in PTL 1 and PTL 2 merely involve simply generating images of a plurality of tomographic planes or slice planes in an object space using the tomosynthesis technique, even while taking into consideration the X-ray energy bin and photon count. That is, X-rays are radiated such as to spread from a spot-like X-ray focal point. However, the differences in concentration among a plurality of tomographic planes attributed to the fan-like spreading of the X-rays and the differences in enlargement ratio attributed to the differences in height from the detection surface of the detector to the plurality of tomographic planes are not mentioned. Therefore, these methods are not configured to enable differentiation between an object that appears in such plurality of tomographic images as a result of the differences in resolution among the tomographic planes, and an extremely fine piece of foreign matter (such as that having a fineness of about 0.3 mm) present inside the object. In addition, determining the detection of foreign matter through visual observation of a plurality of tomographic images is extremely difficult, even should automatic diagnosis with a computer be used.

Therefore, the present invention has been achieved in light of the above-described issues present in conventional X-ray inspection. An object of the present invention is to provide an X-ray inspection apparatus and an X-ray inspection method that enable foreign matter (a substance differing in composition from that of an object) that is present within an object present in an object space to be visualized at a higher resolution, and the presence of such foreign matter to be more easily detected with higher reliability.

Solution to Problem

In order to achieve the object, according to one aspect of the present invention, there is provided an X-ray inspection apparatus, characterized in that apparatus comprises: an X-ray generator provided with an X-ray detector having a point-shaped tube focal spot, the X-ray detector generating an X-ray beam from the tube focal spot, the X-ray beam having a given cone angle in a scan direction and a predetermined fan angle in a direction which is along a section perpendicular to the scan direction; and an X-ray detector provided with a plurality of pixels two-dimensionally arrayed and configured to output at a predetermined frame rate frame data presenting strength of the X-ray beam incident on the pixels, the X-ray detector being arranged to be opposed and separated to and from the X-ray tube with a space provided therebetween, an object being inspected being positioned in the space, wherein either a pair of the X-ray tube and the X-ray detector or the object being inspected is moved relatively to the other in the scan direction, the frame data outputted from the X-ray detector being acquired to inspect an inside state of the object using the acquired frame data. The X-ray inspection apparatus further comprises frame data generating means (52-56) for generating, based on the frame data outputted by the X-ray detector, frame data of each of a plurality of tomographic planes depending on a spread of the fan-shaped X-ray beam and positional differences of the plurality of tomographic planes in a perpendicular direction to the tomographic planes, the tomographic planes being set in the space and parallel to the scan direction; tomographic image generating means (57) for generating tomographic images of the tomographic planes by applying a laminography method to the frame data of the tomographic planes, generated by the frame data generating means; edge information generating means (58-62) for generating a three-dimensional distribution of edge information based on calculating, every pixel of each of the tomographic images, edge information showing changes in pixel values of the respective tomographic images generated by the tomographic image generating means; and combined image generating means (62-63) for generating a single combined image through searching every pixel the three-dimensional distribution of the edge information in a direction passing through the tomographic planes to detect a pixel showing a maximum of the edge information, selecting, at a pixel position corresponding to the detected pixel, only pixels of the tomographic images or other tomographic images generated from the tomographic images, and combining the selected pixels.

Preferably, the frame data generating means, the tomographic image generating means, the edge information generating means, and the combined image generating means are formed integrally in an LSI circuit, which is a hardware circuit such as an FPG (Field Programmable Gate Array), at an output stage of the detector.

Still preferably, the apparatus includes combined image presenting means (23) for visualizing and presenting the single combined image generated by the combined image generating means. Furthermore, the apparatus may include edge information output means (64, 67, 68) for outputting data indicating the three-dimensional distribution of the edge information.

Still preferably, the apparatus may include edge information indexing means (70) for indexing, based on a three-dimensional distribution of the edge information, a profile of the edge information composing the three-dimensional distribution.

Effects of the Invention

In the present invention, frame data of each of a plurality of tomographic planes composing an object space, that is, an inspection space in which an object is placed is generated from X-ray transmission data detected by an X-ray detector. The frame data is generated based on the spreading in the object space of the X-rays radiated from an X-ray tube and the differences in height from a detection surface of the X-ray detector. Tomographic images of the plurality of tomographic planes are generated by a laminography technique being used on the frame data of each of the plurality of tomographic planes. Furthermore, edge information based on the changes in pixel value in each of the plurality of tomographic images is calculated for each of the plurality of tomographic planes and for each pixel. A three-dimensional distribution of the edge information is generated. A search is performed on the edge information in the three-dimensional distribution, for each pixel, in a direction passing through the plurality of tomographic images (such as a direction looking at the focal point of the X-ray tube from each pixel or a direction passing through the plurality of tomographic planes from each pixel). Pixels indicating a maximum value (or a local maximum value) in the edge information are detected. Only the pixels in the tomographic images positionally corresponding to the detected pixels are combined and a single composite image is generated.

That is, the composite image is an image in which, from the plurality of tomographic images, only pixels having the maximum value (or the local maximum value) in the edge information are edited. Therefore, when another substance (a substance having a different X-ray transmission rate from that of the object), such as foreign matter, is present inside the object, the edge, that is, the contour of the substance is emphasized. Furthermore, the substance is in optimal focus in each tomographic plane, the degree of blurring thereof is low, and signal intensity is high.

Therefore, foreign matter, the object to be inspected, and the like in the composite image are visualized with high resolution. That is, the composite image can also be considered to be a radioscopic image in which the object is radioscopically viewed from one direction and only another substance, such as foreign matter, present therein is in optimal focus. When foreign matter or the like is present inside the object in this way, the presence can be more easily detected with higher reliability through the composite image. Furthermore, as a result of data processing performed by the LSI circuit (hardware circuit), the amount of data sent to a central processing unit (CPU) can be reduced, and the frame rate of the X-ray detector can be increased.

BRIEF DESCRIPTION OF DRAWINGS

In the accompanying drawings:

FIG. 20 is a diagram for explaining image addition according to the third embodiment;

FIG. 22 is a diagram for explaining variation examples of a scan trajectory according to each embodiment.

DESCRIPTION OF EMBODIMENTS

Embodiments of an X-ray inspection apparatus of the present invention will hereinafter be described with reference to the accompanying drawings.

First Embodiment

An X-ray inspection apparatus according to a first embodiment is an embodiment describing a basic configuration of the X-ray inspection apparatus of the present invention.

The X-ray inspection apparatus is an apparatus that inspects the presence of foreign matter and the like present inside or on the outer surface of an object to be inspected. The X-ray inspection apparatus performs the inspection using X-ray transmission data obtained by irradiating the object with X-rays.

The X-ray inspection apparatus is provided with an X-ray detecting unit. The X-ray detecting unit includes an X-ray tube that radiates X-rays and a detector that detects X-rays. An object to be inspected passes through a space provided by the X-ray detecting unit, that is, an imaging space through which an X-ray beam passes. The object may, of course, be present in a stationary state within the imaging space, and the X-ray detecting unit may be moved at a fixed speed. In the X-ray detection apparatus, for example, an object that is moving as described above is irradiated with the X-rays. The X-rays that have been transmitted through the object are then detected. An image that shows the inside of the object in a three-dimensional manner is reconfigured from the data of the detected X-rays, through use of a tomosynthesis technique (or a laminography technique) and a technique for focal position search in pixel units.

The X-ray inspection apparatus is capable of inspecting a diverse variety of objects, such as food products, manufactured products, and the human breast. In a specific example described hereafter, an in-line-type food product inspection apparatus will be described. The in-line-type food product inspection apparatus inspects whether or not foreign matter is entrapped inside a food product (for example, vegetables such as green peppers). However, the present invention is not necessarily limited thereto. Regarding food products, the X-ray inspection apparatus is also capable of inspecting for foreign matter such as fishing hooks inside fresh fish. In addition, should the interpretation of the meaning of foreign matter be changed, the X-ray inspection apparatus can also be applied to checking the extent of inclusion of oil and fat content inside meat, the inclusion of foreign matter and bones, cavities and moisture content in lumber, and the like. Regarding manufactured products, the X-ray inspection apparatus can also be applied to checking the mounting state of electronic substrate components, checking the state of connection inside solder bumps, and the like. Furthermore, in mammography in which a human breast is examined, the purpose thereof is discovery of a lesion, such as calcification or a tumor, occurring inside the breast.

Figure 1:
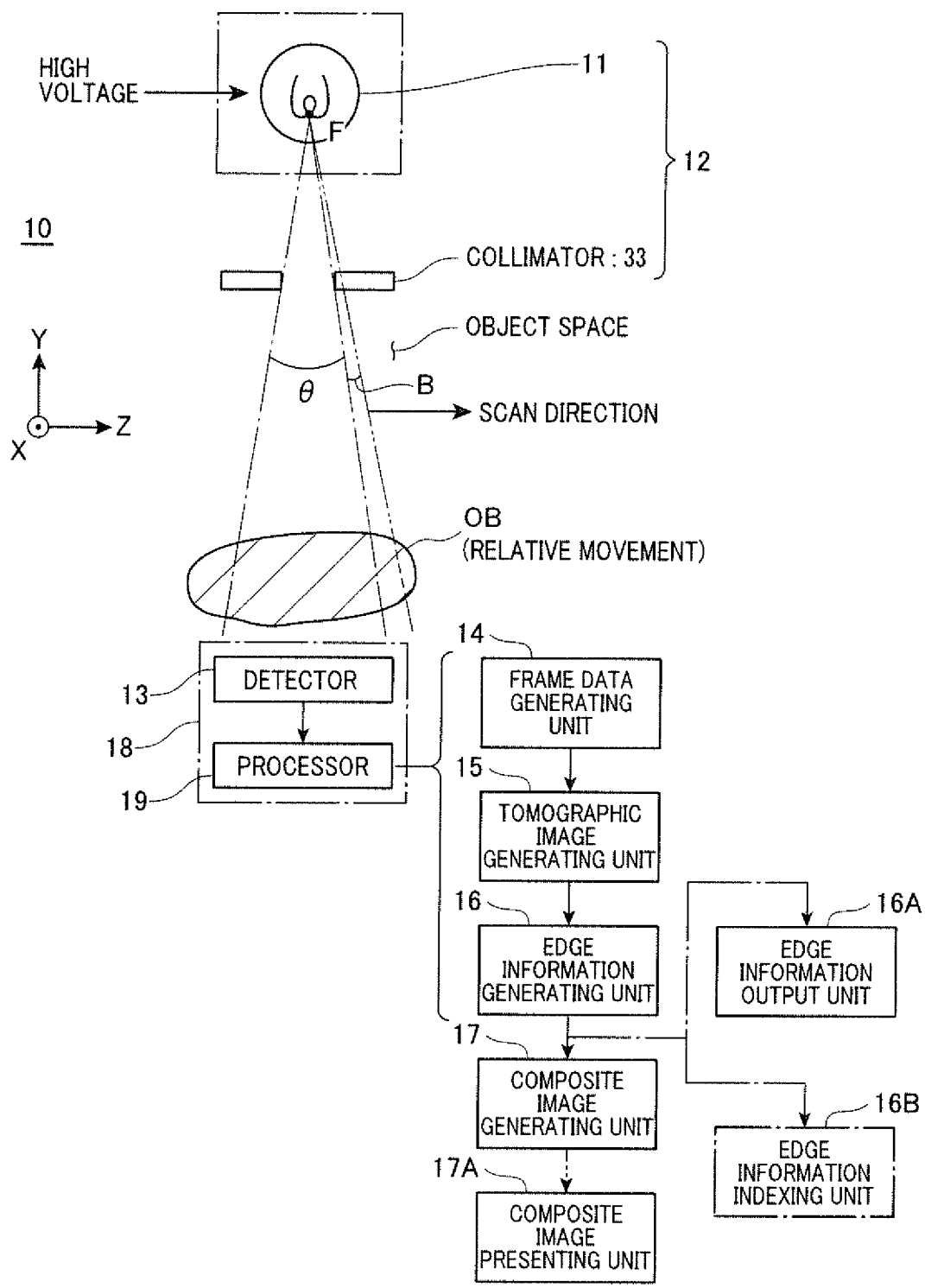
FIG. 1 is a block diagram for explaining an X-ray inspection apparatus of a first example of the present invention, based on a broader concept.

A basic configuration of the X-ray inspection apparatus according to the first embodiment is shown in FIG. 1. As shown in FIG. 1, an X-ray inspection apparatus 10 is provided with an X-ray generator 12 and an X-ray detector 13. The X-ray generator 12 includes an X-ray tube 11 that generates an X-ray beam that has a predetermined cone angle in a scan direction and a predetermined fan angle in a perpendicular direction along a cross-section that is perpendicular to the scan direction. The X-ray detector 13 includes a plurality of pixels in a two-dimensional array and outputs, at every fixed amount of time, frame data indicating the intensity of the X-ray beam incident on each pixel. In the X-ray inspection apparatus 10, an object to be inspected OB is positioned in a space between the X-ray tube 11 and the X-ray detector 13 that is formed when the X-ray tube 11 and the X-ray detector 13 are arranged such as to oppose each other and be separated from each other. The X-ray inspection apparatus 10 collects the pieces of frame data outputted from the X-ray detector 13, while one of either the X-ray tube 11 and X-ray detector 13 pair (that is, the X-ray detecting unit) or the object to be inspected OB is moved in the scan direction in relation to the other. The X-ray inspection apparatus 10 provides information indicating the internal state of the object to be inspected OB by using the frame data.

To provide the information, the X-ray inspection apparatus 10 further includes a frame data generating unit 14, a tomographic image generating unit 15, an edge information generating unit 16, and a composite image generating unit 17. The frame data generating unit 14 serves as a tomographic image generating means. The tomographic image generating unit 15 serves as the tomographic image generating means. The edge information generating unit 16 serves as an edge information generating means. The composite image generating unit 17 serves as a composite image generating means.

Of these units, the frame data generating unit 14 generates frame data of each of a plurality of tomographic planes that are parallel in the scan direction and designated in the space between the X-ray tube 11 and the X-ray detector 13, based on the frame data. The frame data generating unit 14 generates the frame data based on the fan-shaped spreading of the X-rays and the differences in position in the perpendicular direction among the plurality of tomographic planes. The tomographic image generating unit 15 generates tomographic images of the plurality of tomographic planes by applying the laminography technique on the frame data of the plurality of tomographic planes. In addition, the edge information generating unit 16 calculates edge information (such as a primary spatial differential value) that is based on the changes in pixel value in each of the plurality of tomographic images, for each pixel in each of the plurality of tomographic images. The edge information generating unit 16 then generates a three-dimensional distribution of the edge information. Then, the composite image generating unit 17 searches the edge information in the three-dimensional distribution in a direction passing through the plurality of tomographic planes (such as a direction looking at the focal point of the X-ray tube from each pixel or a direction passing through the plurality of tomographic planes from each pixel) for each pixel, for each pixel, and detects pixels indicating maximum values (or local maximum values) in the edge information. 重複しています。 The composite image generating unit 17 generates a single composite image by combining only the pixels in the tomographic images positionally corresponding to the detected pixels.

As an example, the frame data generating unit 14, the tomographic image generating unit 15, the edge information generating unit 16, and the composite image generating unit 17 are mounted in a processing unit 19 that forms an X-ray detection apparatus 18 together with the detector 13.

In the basic configuration, it is particularly preferable that a composite image presenting unit 17A that visualizes and presents the above-described single composite image is provided. In addition, an edge information output unit 16A that outputs data of the three-dimensional distribution of the edge information is preferably provided. Furthermore, an edge information indexing unit 16B that indexes a profile of the edge information composing the three-dimensional distribution, based on the three-dimensional distribution of the edge information, may be provided. A configuration may also be used in which at least any one of the composite image presenting unit 17A, the edge information output unit 16A, and the edge information indexing unit 16B is provided.

Working effects achieved through the basic configuration according to the first embodiment will become clear from the embodiments based on this basic configuration that are described hereafter.

Second Embodiment

Next, an X-ray inspection apparatus according to a second embodiment that more specifically describes an X-ray inspection apparatus 20 according to the above-described first embodiment will be described with reference to FIG. 2 to FIG. 14.

Figure 2:
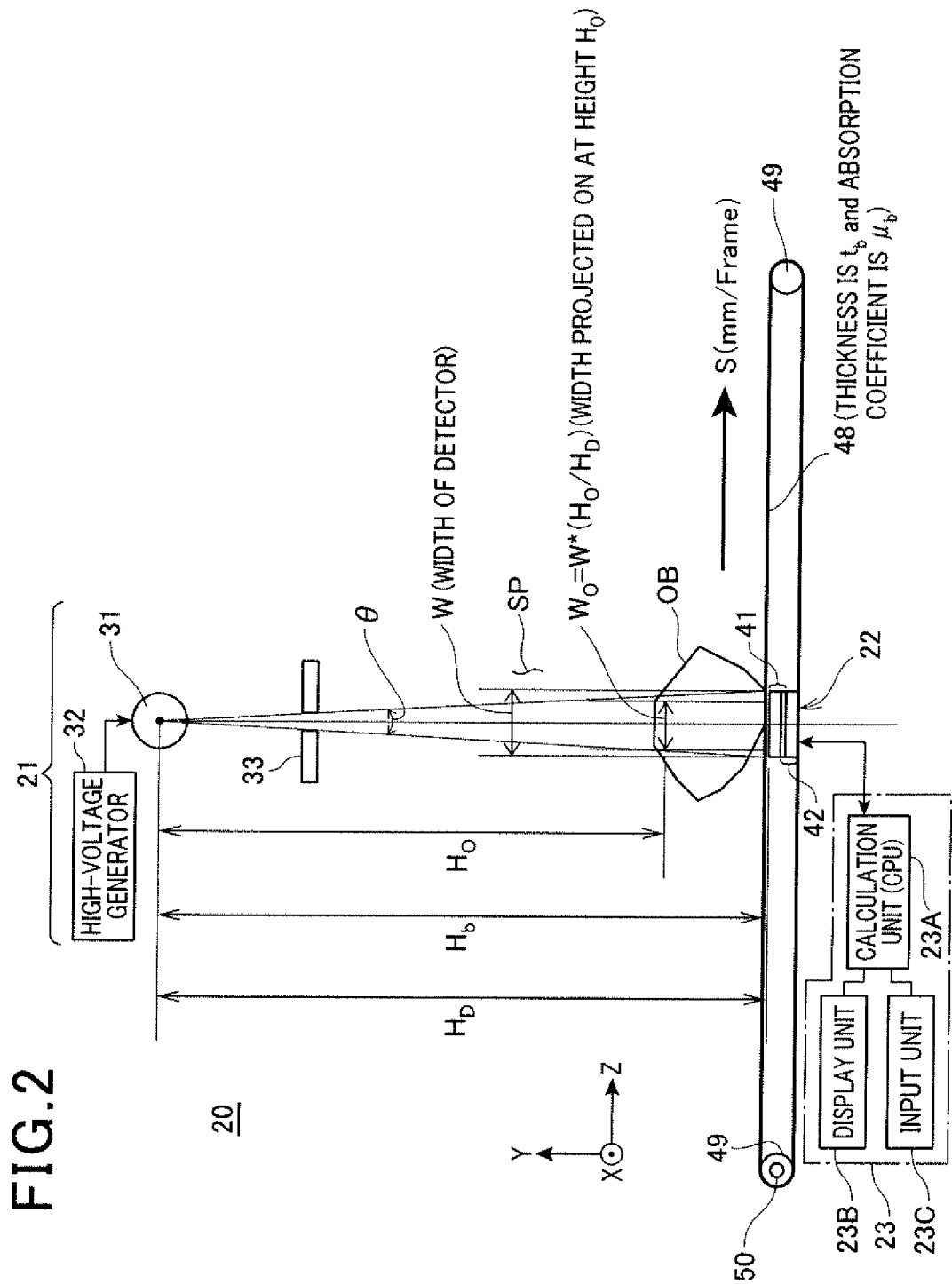
FIG. 2 is an explanatory diagram conceptually showing a more detailed X-ray inspection apparatus of a second example of the present invention.

FIG. 2 shows an overview of a structure of the X-ray inspection apparatus 20 according to the second embodiment. As shown in FIG. 2, as an example, the X-ray inspection apparatus 20 is configured to inspect food products for foreign matter. The X-ray inspection apparatus 20 is an in-line-type X-ray inspection apparatus that generates images of multiple cross-sections of the inside of a food product OB to be inspected, using the laminography technique (also referred to as the tomosynthesis technique). From data of the images of the multiple cross-sections, the X-ray inspection apparatus 20 provides image information indicating various internal structures, Based on the image information, the X-ray inspection apparatus 20 determines whether or not foreign matter is present, determines a three-dimensional position of the foreign matter, and/or identifies (estimates or specifies) the type or the properties of the foreign matter.

The X-ray inspection apparatus 20 includes an X-ray generating unit 21, an X-ray detecting unit 22, and a computer 23. The X-ray generating unit 21 generates X-rays. The X-ray detecting unit 22 is a unit on the X-ray receiving side. The computer 23 is connected to the X-ray detecting unit 22. The computer 23 receives output information from the X-ray detecting unit 22 and processes the received output information. The computer 23 is provided with a calculating unit 23A including a central processing unit (CPU), a display 238, and an input unit 23C. The calculating unit 23A includes a memory 23, such as a read-only memory (ROM) and a random access memory (RAM).

The X-ray generating unit 21 is provided with an X-ray tube 31 and a high-voltage generator 32. The X-ray tube 31 has a spot-like X-ray tube focal point (the focal point diameter being, for example, 1.0 mmφ). The high-voltage generator 32 generates a high voltage necessary for driving the X-ray tube 31 and supplies the high voltage to the X-ray tube 31. Furthermore, the X-ray generating unit 21 includes a collimator 33.

The X-ray detecting unit 22 detects incident X-rays and also integrally handles processing of data on the detected X-rays that is necessary until the image information indicating the internal structure of the object OB is generated. The X-ray detecting unit 22 includes an X-ray detector (referred to, hereafter, as simply a detector) 41 and a data processing circuit 42. The detector 41 detects X-rays, converts the detected X-rays into electrical signals, and outputs the electrical signals. The data processing circuit 42 is electrically connected to an output terminal of the detector 41 and generates the image information from the inputted electrical signals. The processes performed by the data processing circuit 42 compose a part of the characteristics of the present invention. These processes will be described in detail hereafter.

The X-ray tube 31 and the detector 41 are arranged such as to be separated from each other by a fixed distance in a height direction Y. The X-ray tube 31 and the detector 41 both configure an X-ray detecting unit that detects the X-rays that are transmitted through the food product OB. An inspection space (an imaging space or an object space) SP through which the object OB is passed is formed between the X-ray tube 31 and the detector 41 (in physical terms, a conveyor belt described hereafter). Objects OB of various sizes and shapes, such as those in large/small quantities or having a high/low height, pass through the inspection space SP.

The X-rays that are generated from the X-ray tube 31 are formed into an X-ray beam XB by the collimator 33 that is disposed in a predetermined position in the inspection space SR The X-ray beam XB has a predetermined cone angle θ in a scan direction Z and a predetermined fan angle β (see FIG. 12, described hereafter) in a perpendicular direction X along a cross-section that is perpendicular to the scan direction Z.

A conveyor belt 48 passes through the inspection space SR When the direction in which the conveyor belt 48 passes through the inspection space SP is referred to as a conveyance direction of the object OB, this direction corresponds to the scan direction Z of the object OB. When a belt width direction of the conveyor belt 48 is X, an orthogonal coordinate of an X-axis, a Y-axis, and a Z-axis is set as shown in FIG. 2.

The conveyor belt 48 is configured such as to circulate in the scan direction Z (the conveyance direction of the object OB) at a fixed speed S (mm/sec) by a plurality of rollers 49. The rollers 49 are provided with an encoder 50 that detects signals indicating the rotation speed of the rollers, that is, the movement speed of the conveyor belt 48. In this way, the food product OB to be inspected passes through the X-ray beam XB in a traversing manner, in accompaniment with the movement of the conveyor belt 48.

The X-ray detecting unit 22 is disposed between an upper belt portion and a lower belt portion of the conveyor belt 48 (in-line arrangement). An X-ray incidence window of the detector 41 is positioned below the upper belt. At this time, as shown in FIG. 2, the height in the height direction Y from a focal point F of the X-ray tube 31 to the X-ray incidence window of the detector 41 is set to HD. The height in the height direction Y from the same focal point F to the belt portion on the upper side of the conveyor belt 48 is set to Hb.

Figure 3:
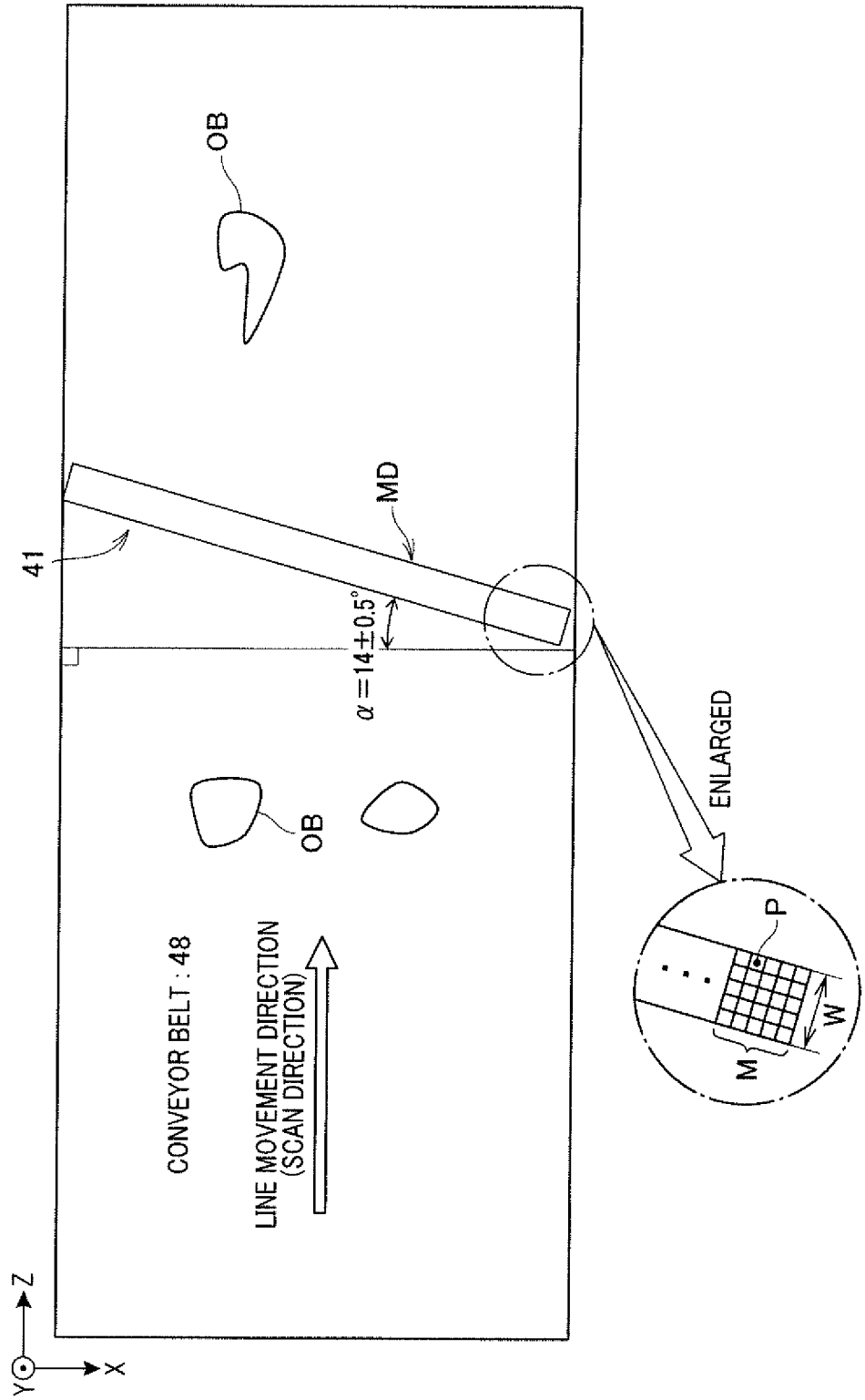
FIG. 3 is a diagram of an example of a belt conveyor and an arrangement of a detector in the X-ray inspection apparatus of the second example.

As shown in FIG. 3, the detector 41 is composed of a plurality of modules M that are connected in a line. As a result, the detector 41 has a narrow, elongated, rectangular contour. In addition, the detector 41, as a whole, has an X-ray incidence window MD (width of the X-ray incidence window MD (detection width)=W) that has a narrow, elongated, rectangular shape.

Each module M is a so-called direct-conversion-type X-ray detection element. In the module M, a detection layer composed of a semiconductor material, such as CdTe or CZT, is formed into, for example, 20×80 pixels (each pixel having a size of 0.2 mm×0.2 mm) P. The module M directly converts X-rays into electrical signals. Although not shown in the drawings, in actuality, a charging electrode and a collecting electrode are respectively adhered on both surfaces of the detection layer that forms the plurality of pixels P. A bias voltage is applied between the two electrodes.

As a result of a total of 29 modules M being arrayed in a vertical column, the above-described X-ray incidence window MD that is about 47 cm in the vertical direction×0.4 cm in the lateral direction (in terms of the number of pixels, 20×2348 pixels, for example) is formed. Therefore, although the plurality of modules M themselves are arrayed in a line, in terms of pixel array, the detector 41 is configured as a two-dimensional direct-conversion-type detector that is narrow and elongated and has a plurality of pixels P in the lateral direction as well.

Figure 4:
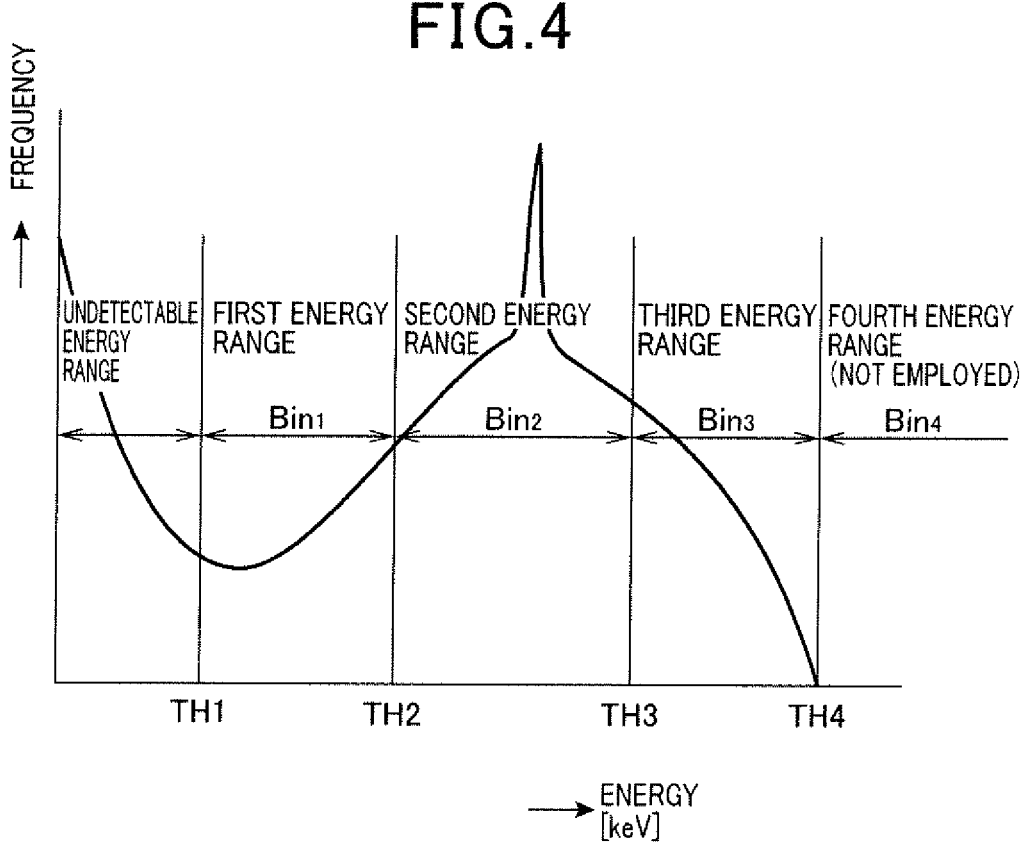
FIG. 4 is a diagram for explaining energy ranges (energy bins) of X-rays.

Furthermore, the detector 41 is a photon-counting-type detector that, under an assumption that X-rays are an aggregation of photons having various energies, is capable of counting the respective number of photons by energy range. As shown in FIG. 4, for example, four energy ranges Bin1 to Bin 4 are set as the energy ranges. Of course, all that is required is that a plurality of number of energy ranges Bin is set.

For each pixel P and for each energy range Bin, the detector 41 detects X-ray intensity, every fixed amount of time, as a counted value (cumulative value) of a digital quantity of the photon count. When a single photon is incident on a certain pixel P, an electrical pulse signal having a peak value that is based on the energy value is generated in the pixel P. Classification of the peak value, that is, the energy value of the electrical pulse signal is performed for each predetermined energy range Bin, and the counted value thereof increases by one. The counted value is collected as the cumulative value (digital value) at every certain amount of time, for each pixel P and for each energy range Bin. The data collection circuit is formed as an application-specific integrated circuit (ASIC) layer on the underside of the above-described detection layer in a stacked state.

As a result of the sampling frequency in the data collection circuit being set to a high value, the cumulative value is collected as the counted value of the digital quantity from each of the 20×2348 pixels, for example, at a frame rate of 6600 fps, for example, and for each energy range Bin.

A direct-conversion-type detector such as this, including the data collection circuit thereof, is publicly known and disclosed in European Patent Publication No. 2674787, for example.

The detector 41 is not necessarily required to be the above-described direct-conversion-type detector. The detector 41 may be a photon-counting detector in which a silicon photomultiplier (SiPM) (also referred to as a multi-pixel photon counter (MPPC)) is configured in a micro-columnar scintillator that has a diameter of approximately several tens of μm, such as a CeLaCl3 detector.

As shown in FIG. 3, the detector 41 is set at an angle to the movement direction of the conveyor belt 48, that is, the scan direction Z (and the belt width direction X). Specifically, when the width of the conveyor belt 48 (width in the X-axis direction) is about 45 cm, the detector 41 has a tilt of β° (such as approximately 14.036±0.5°) in relation to the movement direction of the conveyor belt 48, that is, the belt width direction X perpendicular to the scan direction Z. When the tilt angle α is set such that a diagonal line of the overall four pixels, each of which having a vertical/lateral length ratio of 1:1, that are arrayed in a single row coincides with the scan direction Z, correction of detection data becomes simpler. In this way, the square-shaped contour of each pixel P is also arrayed such as to be tilted at an angle in relation to the belt width direction X (and the scan direction Z).

When this tilted arrangement is not used, that is, when the detector 41 is arranged such that the long direction thereof is parallel to the belt width direction X, the gaps (ordinarily 200 μm) between the pixels P face the scan direction Z, and a portion from which data is not collected occurs in the object OB. However, as a result of the detector 41 being arranged at an angle as described above, this portion from which data is not collected is no longer present. In addition, when conversion (affine transform) is performed on an axis composed of pixels based on a reconfiguration space, that is, an object space at the time of scanning, as described hereafter, a pixel value is determined from a plurality of nearby pixels based on a subpixel technique. Therefore, an effect is achieved in which various factors for variations among pixels (such as variations in manufacturing precision of pixels and photon noise) can be suppressed. As a result, an image with less noise can be generated.

The size and shape of the opening of the collimator 33 is designed such that the X-rays are exactly irradiated onto an effective area of the detection surface of the detector 41 (not shown). Of course, when the configuration is such that the distance between the X-ray tube and the detector is variable, the size and shape of the opening of the collimator 33 is controlled under instructions from the computer 23. As a result, the collimator 33 gives the X-ray beam XB the above-described cone angle θ and fan angle β. Meanwhile, the detector 41 according to the present embodiment is arranged at an angle to the orthogonal coordinate system set in relation to the scan direction Z, as described above. Therefore, the opening of the collimator 33 is set taking into consideration this tilted arrangement. That is, because the X-ray incidence window MD of the detector 41 is also positioned at an angle to the orthogonal coordinate system, the radiation field onto the detector 41 is set to match the contour on the X-ray incidence window MD.

Figure 5:
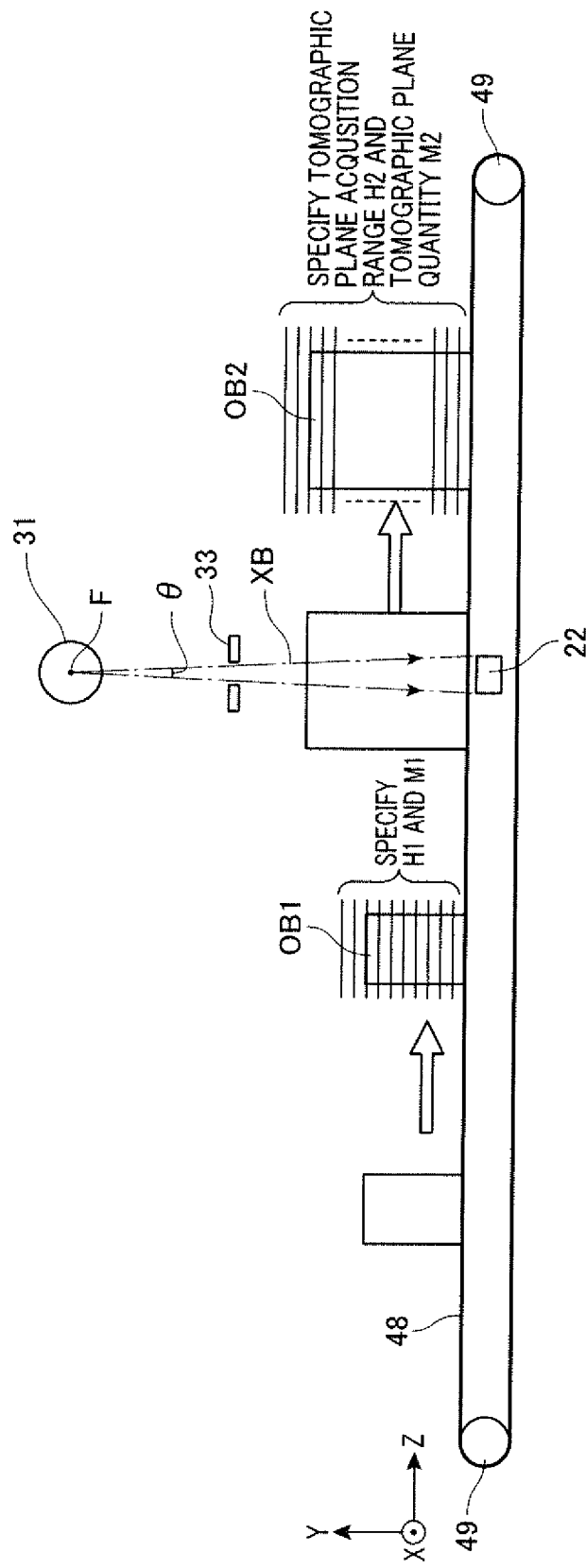
FIG. 5 is a diagram for explaining a relationship among the size of an object to be inspect, a tomographic plane acquisition range, and a tomographic plane quantity.

FIG. 5 schematically shows a positional relationship between the X-ray beam XB and the food product OB serving as an object to be inspected, along the scan direction Z. The food product OB is placed on the conveyor belt 48 and conveyed in the scan direction Z. The food product OB passes through the X-ray beam XB in a traversing manner. The food product OB naturally has, to some extent, a length in the height direction Y. The X-ray beam XB has the predetermined cone angle θ in the scan direction Z. Therefore, as schematically shown in FIG. 5, when observed from the direction opposing the YZ plane, the radiation width of the X-ray beam XB in the scan direction Z decreases as the X-ray beam XB becomes closer to the X-ray tube 31.

In the X-ray inspection apparatus 20 according to the present embodiment, an operator is able to selectively designating a tomographic plane acquisition range and the number of tomographic planes, based on the height of the object OB in the inspection space SR The tomographic plane acquisition range indicates an inspection range in the height direction Y. The tomographic plane acquisition range may also be simply referred to as an imaging range in the height direction Y.

The tomographic plane mentioned herein refers to a plane at a certain height. As the interval between tomographic planes is set to be narrower, the resolution of foreign matter detection, described hereafter, increases. However, by this extent, the size of the circuit handling the detection process also increases.

An explanation with reference to the example in FIG. 5 is as follows. Regarding an object OB1 that is low in height, a tomographic plane acquisition range H1 and a tomographic plane quantity M1 can be designated. In addition, regarding an object OB2 that is high in height (the height of OB2>the height of OB1), when the thickness of each tomographic plane is set to be common across all objects OB (OB1 and OB2), a tomographic plane acquisition range H2 (>H1) and a tomographic plane quantity M2 (>M1) can be designated. The operator may selectively designate arbitrary values each time, via the computer 23, for the tomographic plane acquisition range and the tomographic plane quantity. Alternatively, the tomographic acquiring range and the tomographic plane quantity may be set to default values. The range of height of the object OB may be automatically detected or estimated at the incidence of the apparatus 20, and the tomographic acquiring range and the tomographic plane quantity may be automatically set based on the obtained value.

Multiple tomographic planes are virtually set in the height direction Y in this way. Therefore, in the inspection space SP, the width in the scan direction Z (that is, the radiation field) of the X-ray beam XB that is transmitted through each of the multiple tomographic planes differs with each cross-section. A basis of the X-ray inspection apparatus 20 is that image reconfiguration of each of the multiple tomographic planes is performed. Therefore, data processing cannot be performed while ignoring the difference in width of the X-ray beam XB among the tomographic planes.

An explanation of the foregoing with reference to above-described FIG. 2 is as follows. When image reconfiguration, described hereafter, is performed on an arbitrary tomographic plane (the thickness being ignored for now) $H_O$, X-ray absorption per unit length of the tomographic plane increases in value by an amount equivalent to $H_D/H_O$. A reason for this is that the X-ray beam XB is continuously enlarged from the spot-like X-ray tube focal point F (focal point diameter: 1 mm) of the X-ray tube 31 towards the width W (such as 4 mm) of the X-ray incidence window MD of the detector 41. That is, the actual detector projection width $W_O$ of the arbitrary tomographic plane $H_O$ is $W_O = W \cdot (H_O/H_D)$.

Therefore, the X-ray transmission data detected by the detector 41, that is, the frame data) is required to be corrected in the height direction Y. In other words, regarding the height direction Y, the effect of the enlarged projection attributed to the spreading of the X-ray beam XB (that is, the X-ray beam XB having the cone angle θ in the scan direction Z) directly remains as the magnitude of the pixel density value in the detected transmission data. Therefore, regarding this effect, correction of the density value is necessary after collection. Specifically, a correction is performed in which a coefficient is multiplied with HO/HD and the value of each pixel in each tomographic plane.

Meanwhile, regarding the scan direction Z, when processing is performed to reset the pixel sizes in the detected X-ray transmission data to the same value, the density value of each pixel is not required to be corrected based on the tomographic plane height. A reason for this is that a movement speed S (the speed of the conveyor belt 48) in the scan direction Z is a fixed value regardless of height. The effective width of each tomographic plane for the transmission data detected by the detector 41 is merely uniformly compressed to HO/HD. Therefore, regarding the scan direction Z, even should there be a difference in the height direction Y, the pixel density in the detected transmission data is not required to be corrected.

Furthermore, regarding the direction perpendicular to the scan direction (that is, the direction X of the belt width in FIG. 3), a process is performed to reset the pixels such that the pixel size decreases as the pixel size approaches the X-ray tube 31 (that is, as the position of the tomographic plane becomes higher in the Y-axis direction that is the height direction). As a result, correction of the pixel value (density value) is also not necessary in the direction perpendicular to the scan direction. In this way, regarding the scan direction Z and the direction X perpendicular thereto, density correction of the pixels is not required because of adjustment of the pixel size. Therefore, all that is required is that density correction be performed for the height direction Y.

Moreover, because the conveyor belt 48 is used in the X-ray inspection apparatus 20, it is also necessary to consider to the necessity of correction resulting from the belt 48. When a certain object OB is conveyed on the conveyor belt 48 that has a fixed thickness, the X-ray beam is transmitted through the object OB and a portion of the conveyor belt 48. However, the relationship between the thicknesses (heights) of both the object OB and the conveyor belt 48 in the height direction U does not change at any tomographic position. Therefore, the effect of the presence of the conveyor belt 48 is fixed at any tomographic plane position in the height direction Y. As a result, the degree of influence in the height direction attributed to the presence of the conveyor belt 48 does not differ. That is, although correction of X-ray absorption attributed to the conveyor belt 48 is required, there is no difference caused by height.

<Regarding the Data Processing Circuit>

Next, the data processing circuit 42 that is integrally formed with the detector 41 will be described with reference to FIG. 6.

The data processing circuit 42 is provided as an element on the X-ray detecting unit side and is also a characteristic of the present example. The data processing circuit 42 is integrally formed by a large-scale integration (LSI) circuit, such as a field-programmable gate array (FPGA), in the output stage of a data collection circuit 41A (see FIG. 6) of the above-described detector 41. That is, often seen in the past, the data processing circuit 42 is characterized by being capable of performing calculation with high immediacy at an extremely high speed, without depending on software processing by the CPU. Of course, should the environment allow for increase in calculation load on the CPU, a program for the CPU may be set such as to actualize the processes performed by the circuit group, described hereafter, by software.

Figure 6:
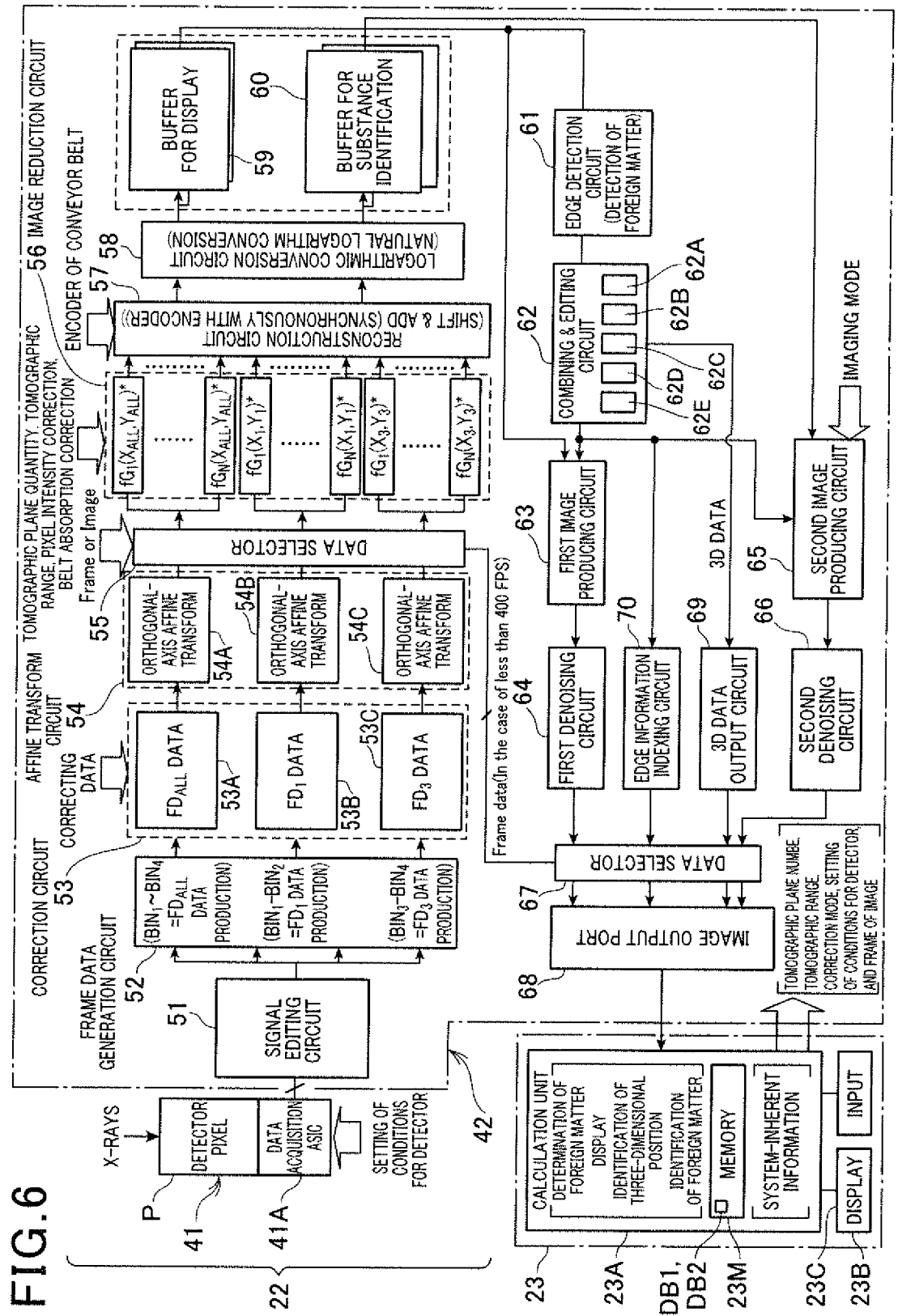
FIG. 6 is a block diagram for explaining a configuration of a data processing circuit that is integrally formed with the detector in the X-ray inspection apparatus.
Figure 7:
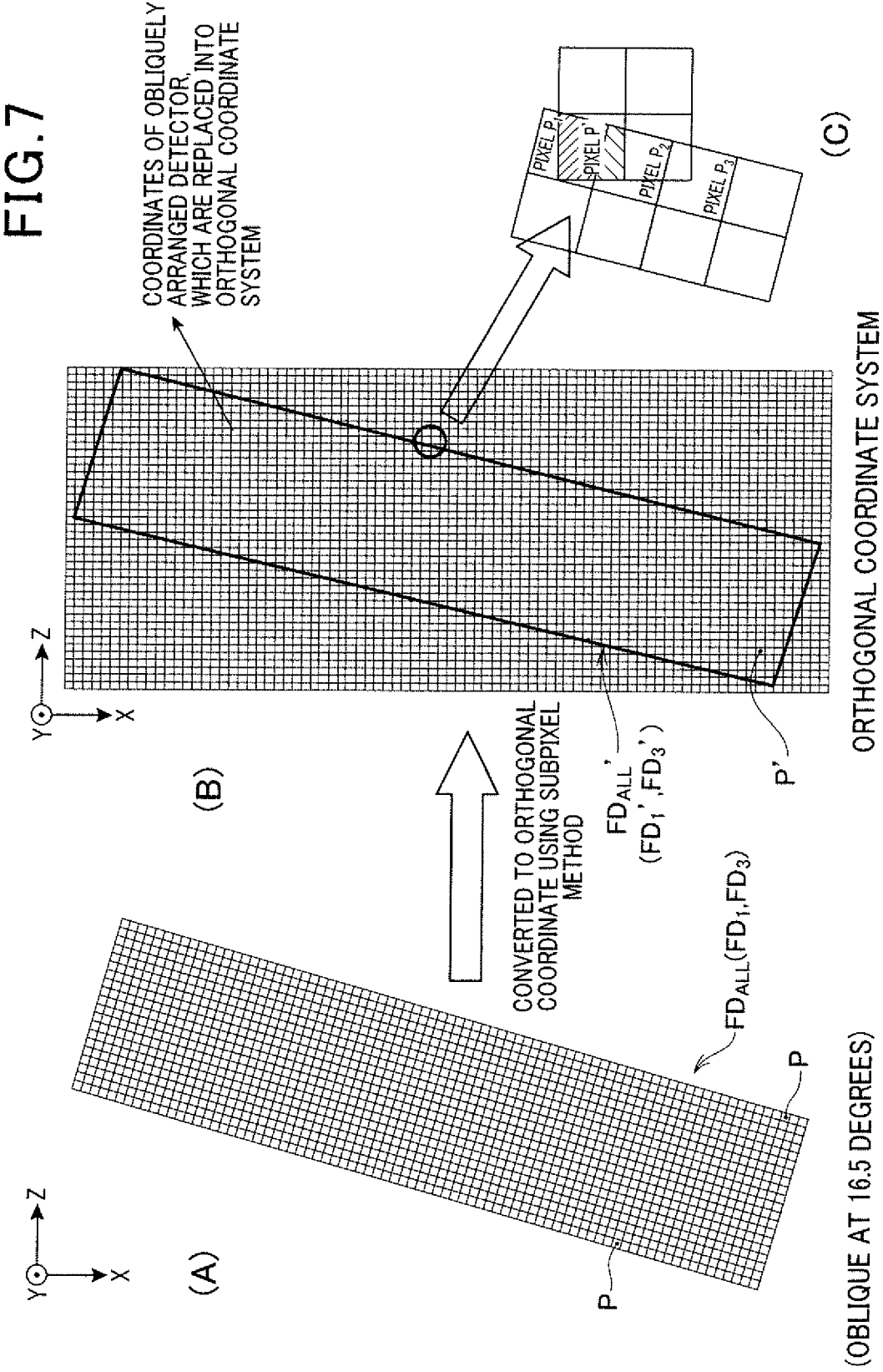
FIG. 7 is a diagram for explaining resetting of pixels onto an orthogonal coordinate system, accompanying placement of the detector at an angle to a scan direction.
Figure 8:
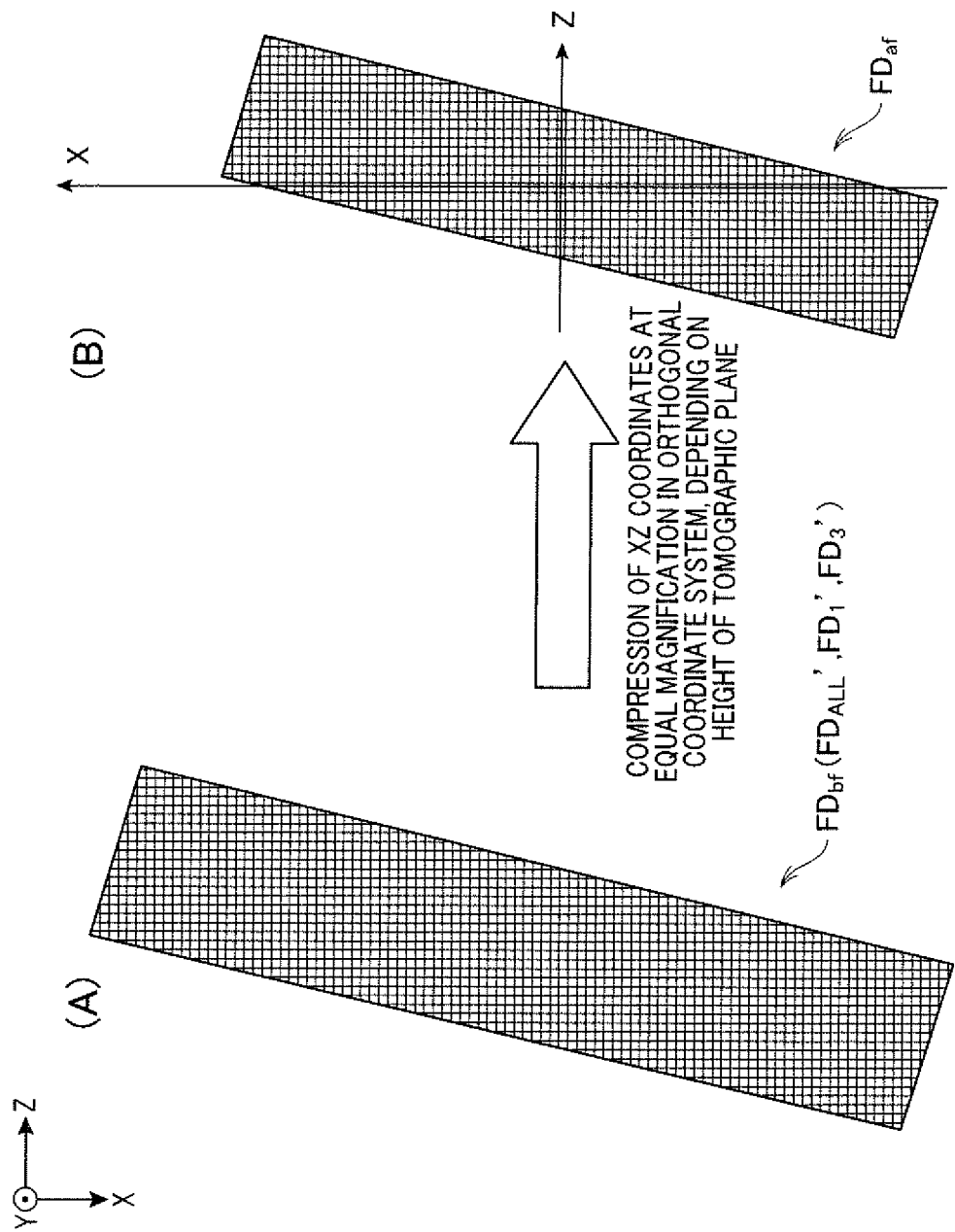
FIG. 8 is a diagram for explaining a process for reducing collected frame data based on the height of a tomographic plane.

As shown in FIG. 6, the data processing circuit 42, which is composed of the FPGA, is disposed between the detector 41 and the computer (personal computer (PC)) 23 that serves as a portion of a console. The data processing circuit 42 includes a signal editing circuit 51 that is connected to the output terminal of the detector 41. On the output side of the signal editing circuit 51, a frame data generation circuit 52, a correction circuit 53, an affine transform circuit 54, a data selector 55, an image reduction circuit 56, a reconfiguration circuit (shift-and-add circuit) 57, and a logarithmic conversion circuit 58 are provided in this order.

Furthermore, a buffer for display 59 and a buffer for substance identification 60 also additionally provided at the output terminal of the logarithmic conversion circuit 58. Of these buffers, the buffer for display 59 leads to an edge detection circuit for detecting foreign matter, a combining and editing circuit 62, a first image generation circuit 63, and a first de-noising circuit 64.

The output from the combining and editing circuit 62 further additionally includes a path that passes through a second image generation circuit 65 and reaches a second de-noising circuit 66.

The respective outputs (de-noised image data and tomographic plane information) of the first and second de-noising circuits 64 and 66 reach an image output port 68 via a data selector 67, and are connected to the above-described computer 23 via the output port 68. Furthermore, a three-dimensional (3D) data output circuit 69 and an edge information indexing circuit 70 are also interposed between the combining and editing circuit 62 and the data selector 67.

[Data Processing Unique to the Present Embodiment]

The above-described data processing circuit 42 will be described in detail hereafter.

As shown in FIG. 6, the signal editing circuit 51 is connected to the output of the data collection circuit 41A of the detector 41. Digital data is serially outputted from the output terminal of the data collection circuit 41A at a high speed (such as 6600 FPS). The digital data indicates the counted value (cumulative value) of the X-ray photons for every fixed amount of time that is collected for each pixel P and for each energy range Bin (see FIG. 4). The signal editing circuit 51 receives the serial digital data and edits the received digital data to data for each energy range Bin, for all of the pixels P of the detector 41. The signal editing circuit 51 then outputs the edited data. That is, the signal editing circuit 51 successively outputs, as raw frame data, the counted value of X-ray photons that have been counted in each of the energy ranges Bin1, Bin2, Bin3, and Bin4, for each of the pixels P. The raw frame data is, for example, composed of 20×2348 pieces of pixel data, and successively outputted at a cycle of a fixed amount of time for each energy range Bin.

The raw frame data is outputted to the frame data generation circuit 52 in the next stage. The frame data generation circuit 52 uses the successively received raw frame data and calculates each of:

composite frame data $FD_{ALL}$ obtained by adding, for each pixel, the pixel values of the pixels P respectively corresponding to the four energy ranges, that is, the energy ranges Bin1 to Bin4;

first energy range frame data $FD_1$ obtained from the difference between the pixel value of the raw frame data of the energy range Bin2 that is second from the bottom and the pixel value of the raw frame data of the energy range Bin1 that is first from the bottom; and third energy range frame data $FD_3$ obtained from the difference between the pixel value of the raw frame data of the energy range Bin4 that is fourth from the bottom, that is, the uppermost energy range, and the pixel value of the raw frame data of the energy Bin3 that is third from the bottom.

Of these pieces of frame data, the composite frame data $FD_{ALL}$ is used for X-ray inspection. The first and third energy range frame data $FD_1$ and $FD_3$ are data used for so-called substance identification in which the type and/or properties of foreign matter is identified (estimated or specified). Through use of the difference, the amount of error from erroneous counting in the higher energy ranges resulting from superposition phenomenon (pile-up) among X-ray photons incident on each pixel X can be suppressed.

As shown in FIG. 7(A), the composite frame data $FD_{ALL}$, and the first and third energy range frame data $FD_1$ and $FD_3$ are tilted by $\alpha°$ (substantially $14.036\pm0.5°$ in this example) in relation to the X axis of the two-dimensional orthogonal coordinates of the XZ plane.

The three types of frame data $FD_{ALL}$, $FD_1$, and $FD_3$ outputted from the frame data generation circuit 52 are each sent to the m correction circuit 53 in the next stage. The correction circuit 53 includes separate composite frame correction circuit 53A, first difference correction circuit 53B, and second difference correction circuit 53C. These correction circuits 53A to 53C are provided with correction data from the system side. The correction data is data for correction of dead pixels that are known in advance on the system side, correction regarding density (intensity), correction regarding evenness in pixel values, and the like. As a result, the correction circuits 53A to 53C perform correction processes for each piece of frame data and for each pixel using publicly known techniques, such as weighting calculation. The correction regarding density also includes processes such as adding a different weight to the frame data for each energy range of the X-rays and emphasizing a specific X-ray energy range.

The frame data $FD_{ALL}$, $FD_1$, and $FD_3$ are each sent to the affine transform circuit 54 in the next stage. In correspondence to the three types of frame data, the affine transform circuit 54 also includes three affine transform circuits 54A to 54C, as hardware circuits, for the composite frame data, and for the first and second difference frame data. Each affine transform circuit 54A (to 54C) converts the tilted frame data $FD_{ALL}$ ($FD_1$, $FD_3$) shown in FIG. 7(A) to the orthogonal coordinates on the X-Z axis based on the subpixel method.

Frame data $FD_{ALL}'$ ($FD_1'$, $FD_3'$) that has undergone the affine transform is schematically shown in FIG. 7(B). In the subpixel method, the pixel value of each pixel P' on the orthogonal coordinates is expressed by a sum of the multiplication values of the ratios of the pixel values of a plurality of pixels related to the tilted frame data $FD_{ALL}$ ($FD_1'$, $FD_3'$) that occupy the pixel P', to the area occupancies of the pixels. In other words, in the case of the example in FIG. 7(C), $P'=p1 \times r1 + p2 \times r2$. Here, p1 and p2 are the pixel values of pixels P1 and P2. In addition, r1 and r2 are the area values. In the instance of the pixel P' shown in FIG. 7(C), because the pixel P' is an end portion of the tilted frame data, $r1+r2=r12$ (<1). This is used as a substitution value herein.

For each transform system, the pieces of frame data $FD_{ALL}'$, $FD_1'$, and $FD_3'$ are successively sent to the data selector 55 at a fixed interval. The data selector 55 creates a set of frame data while temporarily collecting the pieces of frame data in an internal memory thereof. As a result, sets of frame data for image reconfiguration are individually formed for the composite frame data $FD_{ALL}'$, the first energy range frame data $FD_1'$, and the third energy range frame data $FD_3'$.

The data selector 55 can also receive command information that indicates whether to use the frame data (including the energy range of the frame data to be used) or image data. Based on the command information, the data selector 55 can selectively output the set of composite frame data $FD_{ALL}'$, the set of first energy range frame data $FD_1'$, and the set of third energy range frame data $FD_3'$. For example, when the command information indicates foreign matter detection, the data selector 55 can output only the set of composite frame data $FD_{ALL}'$ to the image reduction circuit 56 in the next stage. Meanwhile, when the command information indicates substance identification of the object OB, the data selector 55 can selectively output only the set of first energy range frame data $FD_1'$ and the set of third energy range frame data $FD_3'$. Of course, when the command information indicates both foreign matter detection and substance identification, the data selector 55 can output all of the three types of frame data sets.

The image reduction circuit 56 handles two processes. A first process is a process in which each of the set of composite frame data $FD_{ALL}'$, the set of first energy range frame data $FD_1'$, and the set of third energy range frame data $FD_3'$ outputted from the data selector 55 is reduced based on the height of each tomographic plane in the height direction Y that is determined from the tomographic plane acquisition range H and the tomographic plane quantity M that are designated in advance. Specifically, as shown in FIG. 8(A) to FIG. 8(B), frame data $FD_{af}$ is generated by the size of each pixel of each piece of frame data $FD_{bf}$($FD_{ALL}'$, $FD_1'$, and $FD_3'$) being compressed at equal magnification in the Z-axis direction and the X-axis direction based on the height of each tomographic plane. Although not shown in the drawings, in the image reduction circuit 56, circuit elements for the reduction process are mounted in parallel such as to amount to the total number of tomographic planes of the three types of frame data sets (not shown). The width in the X-axis direction of each tomographic plane is configured to match the width formed by the fan angle $\beta$ of the radiated X-rays.

A second process of the image reduction circuit 56 is resetting of pixel size in the reduced frame data $FD_{af}$, described above, and mapping. In other words, the image reduction circuit 56 resets the pixel size in the frame data $FD_{af}$ to the pixel size in the original frame data, that is, the frame data detected through the detection surface (X-ray incidence window MD) of the detector 41 (that is, the size of the pixel P itself of the detector 41, and also referred to as the original pixel size). This resetting is performed such that the pixel positioned at the center of the reset frame data, that is, the pixel positioned at the center in each of the Z-axis direction and the X-axis direction matches the pixel positioned at the center of the original frame data on the detection surface, in terms of position on the XZ plane.

That is, after the center pixel in the Z-axis direction and the X-axis direction is positioned such that the positions in the frame data before and after the resetting match, the pixel value of each pixel in the reset frame data is calculated.

The first and second processes are performed by each circuit element (not shown) of the image reduction circuit 56. When these processes are generally expressed, a process expressed by the following expression is performed on each pixel in the frame data.

$$*fG_i(Z_j, X_j)$$

Here, i=1 to N (N: the number of tomographic planes), and j=ALL, 1, or 3

(j=ALL is for the process on the set of composite frame data;

j=1 is for the process on the set of first energy range frame data; and j=3 is for the process on the set of third energy range frame data).

The expression means that the pixel positioned at "Zj, Xj" is reduced at least by a function Gi of the height of the tomographic plane, and each pixel is again reset to the pixel size in the original frame data in only the scan direction by a function f. The function Gi reflects the designated tomographic plane range, the tomographic plane quantity, the density correction in the height direction Y, and furthermore, a factor amounting to X-ray absorption correction for the conveyor belt 48 that is used.

Resetting of the pixel size in the frame data $FD_{af}$ is not necessarily limited to when the resetting to the pixel size in the original frame data (original pixel size) is performed. For example, the pixel size may be smaller than the pixel size in the original frame data or may be a pixel size having a desired resolution. The resetting size being set to the same value as the original pixel size is an example.

Figure 9:
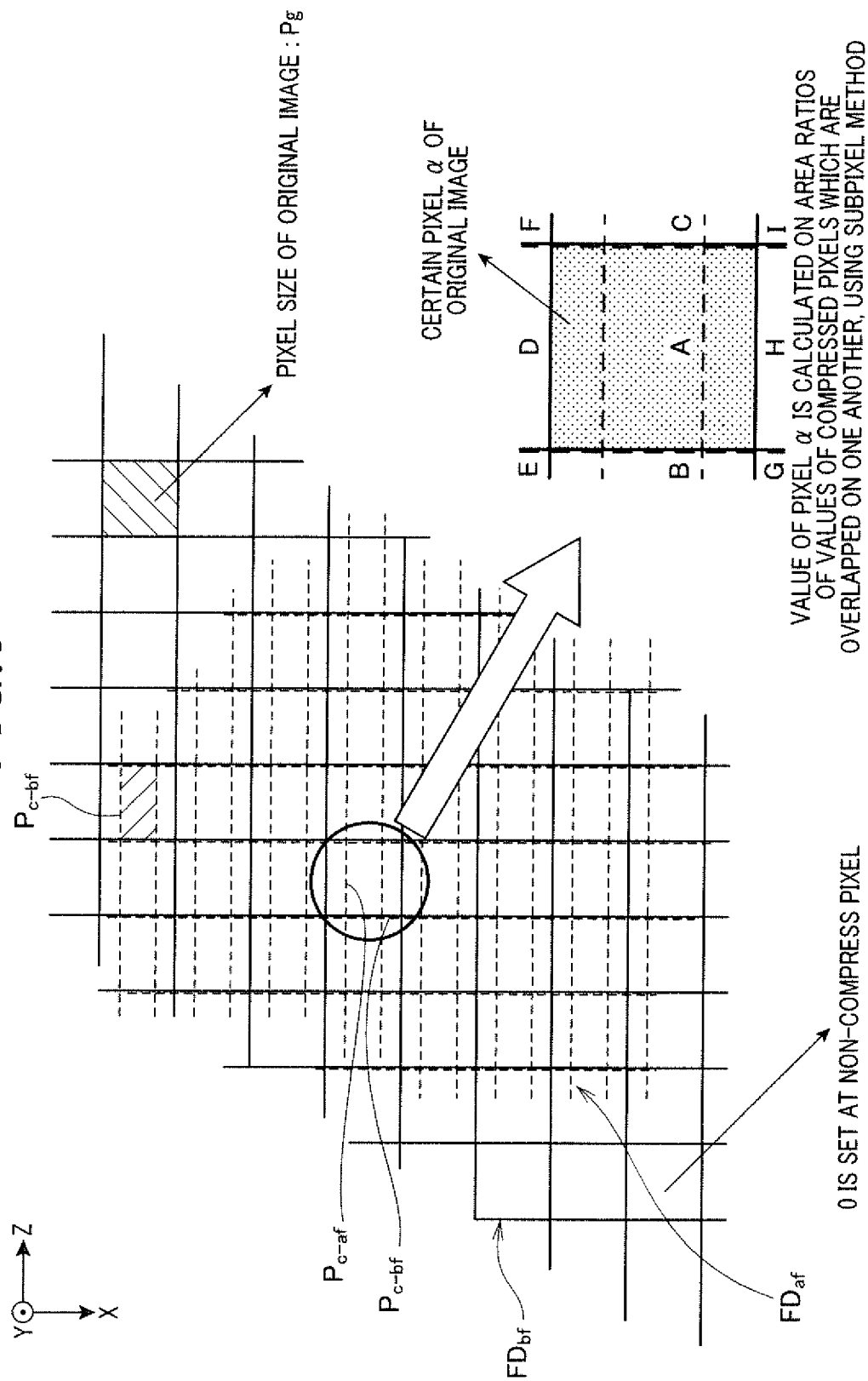
FIG. 9 is a diagram for explaining a process for resetting reduced frame data to the size of the pixels in the detector, that is, the so-called original image pixels.
Figure 10:
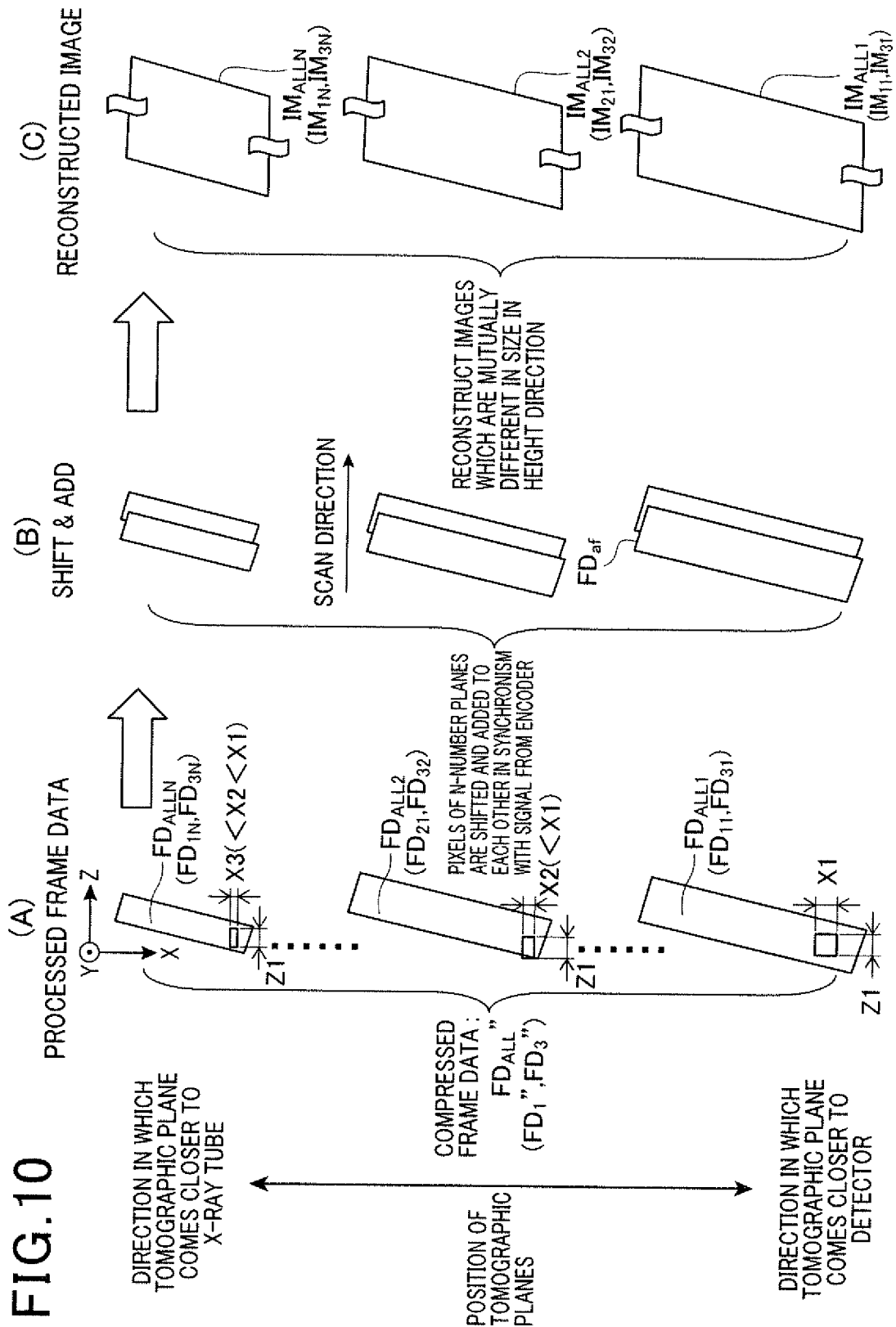
FIG. 10 is a diagram for explaining combining and editing of reconfigured images.
Figure 11:
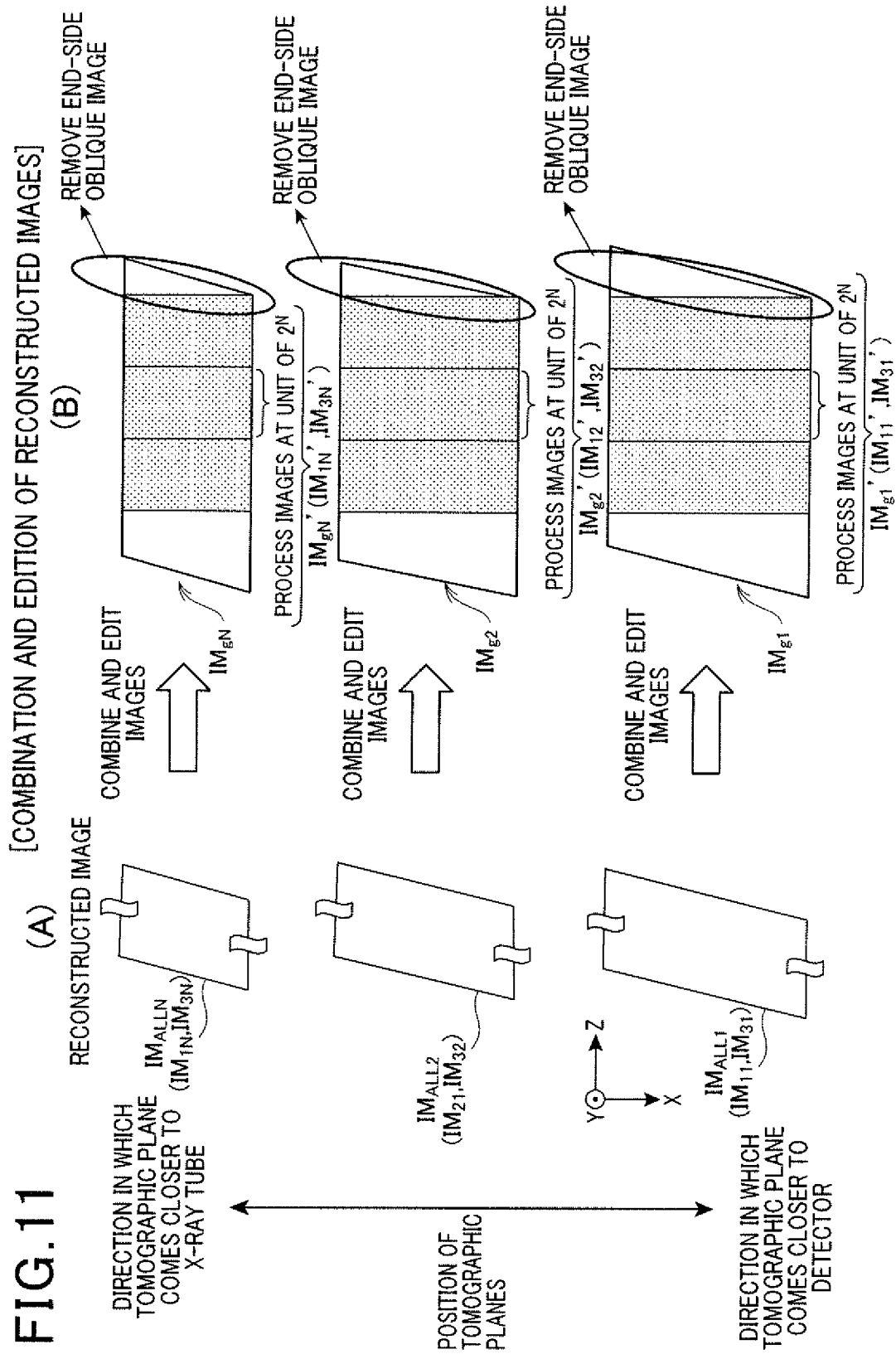
FIG. 11 is a diagram for explaining image reconfiguration.

FIG. 9 schematically shows the process for resetting pixels. In FIG. 9, the original frame data is indicated by solid lines $FD_{bf}$, and the frame data after reduction by equal magnification is indicated by dotted lines $FD_{af}$. In the resetting of pixel size, in addition to the change in pixel size, the pixel value is calculated by the subpixel method, based on the overlap between the pieces of frame data. The resetting of pixel size is performed by pixels $P_{c-bf}$ and $P_{c-af}$ that are positioned at the center in the X-axis direction and the Z-axis direction in the two pieces of frame data being matched.

In this way, the image reduction circuit 56 reduces each piece of frame data $FD_{af}$ detected on the detection surface (X-ray incidence window MD) of the detector 41 based on the height of the designated plurality of tomographic planes. In addition, while matching the position of the center pixel between the pieces of frame data before and after reduction, the image reduction circuit 56 performs conversion to frame data in which the pixel size is the same as the original pixel size in only the scan direction, before and after reduction.

As a result, each of the plurality of pixels in each piece of frame data is a square having a size that is the same as the original pixel size in the lowermost tomographic plane. However, as the position of the tomographic plane becomes higher, the pixel forms a rectangle of which the length in the direction perpendicular to the scan direction becomes shorter. As the position of the tomographic plane becomes higher, the rectangle becomes more elongated and narrow. However, the numbers of pixels composing the plurality of tomographic planes are the same among the tomographic planes.

This aspect is schematically shown in FIG. 10(A). The pixels in frame data $FD_{ALL1}$ of a tomographic plane positioned at the bottom in the height direction (Y-axis direction) has the original pixel size of a square (vertical×lateral=X1× Z1 and X1=Z1). Conversely, the pixel in frame data $FD_{ALL2}$ of a tomographic plane that is positioned at a height near the middle has a pixel size of a rectangle (vertical×lateral=X2× Z1 and X2<X1). Furthermore, a pixel of frame data $FD_{ALLN}$ of a tomographic plane that is positioned even higher is a pixel size of a rectangle (vertical×lateral=X3×Z1 and X3<X2).

In this way, frame data $FD_{ALL}"$, or $FD_1"$ and $FD_3"$ in which, while the pixel sizes in the scan direction in the frame data are the same as one another, the pixel sizes gradually decrease as the position of the tomographic plane becomes higher (Y-axis direction) to be perpendicular (X-axis direction) to the scan direction is sent to the reconfiguration circuit 57 in the next stage. The reconfiguration circuit 57 performs a process involving the known laminography technique (also referred to as the tomosynthesis technique), that is, a shift and add process, by an amount of shifting that is synchronous with the conveyance speed from the encoder 50, on a plurality of designated pieces of frame data $FD_{ALL}"$, for example. As a result, the reconfiguration circuit 57 reconfigures a single piece of tomographic image data $IM_{ALL}$ (:$IMA_{LL1}$ to $IM_{ALL}N$) from the designated number of pieces of frame data $FD_{ALL}"$ (see FIGS. 10(B) and (C)). The frame data to be processed is successively changed. Therefore, in accompaniment with the conveyance of the object OB, the data of the reconfigured tomographic image $IM_{ALL}$ is generated at every fixed amount of time. As described above, the position of the tomographic plane in the height direction Y becomes higher as the tomographic image $IM_{ALL}$ advances upwards from the bottom level in FIG. 10 to the middle level and to the top level. Therefore, as the tomographic image $IM_{ALL}$ advances upwards in FIG. 10, the size of the reconfigured tomographic image becomes smaller by the reduction process.

In a similar manner, regarding the first and third energy range frame data $FD_1"$ and $FD_3"$, planar images IM1 (IM11, . . . IM1N) and IM3 (IM31, IM3N) that are reconfigured based on the frame data of a specific X-ray energy range are respectively reconfigured, as described hereafter.

These pieces of tomographic image data IM are converted to natural logarithmic tomographic image data by the logarithm conversion circuit 58. The data of the tomographic images IM are further sent to the buffer for display 59 and the buffer for substance identification 60 for foreign matter detection.

Of these components, the buffer for display 59 and the buffer for substance identification 60 both have a configuration of a double buffer. The configuration is such that, by writing and reading of data to and from the double buffer being controlled, combining and editing of the reconfigured tomographic images IM is performed. As shown in FIG. 11(A), the buffer for display 59 and the buffer for substance identification 60 are successively provided, in time series, with the reconfigured tomographic images $IM_{ALL}1$ to $IM_{ALL}N$ (IM11 to IM1N; IM31 to IM3N) that differ in image size depending on the height of the tomographic plane.

Of these buffers, in the buffer for display 59, a plurality of first tomographic images $IM_{ALL}1$ are written such as to be aligned side by side in a two-dimensional manner, in a memory region thereof. That is, the plurality of tomographic images $IM_{ALL}1$ are combined to form a composite tomographic image IMg1 that forms a parallelogram. Next, as shown in FIG. 11(B), data of a single rectangular area image IMg1', or a plurality thereof, is read from the parallelogram composite tomographic image IMg1 in, for example, the lateral-axis direction in units of 2N (N=1, 2, . . . ). The unit of data readout is not necessarily limited to 2N (N=1, 2 . . . ). A desired size unit may be selected.

The combining process is similarly performed in parallel on the second to N-th tomographic images $IM_{ALL}2$ . . . $IM_{ALL}N$. As a result, in a similar manner, the data of rectangular area images IMg2 to IMgN are respectively generated from the composite tomographic images IMg2 to IMgN.

Figure 12:
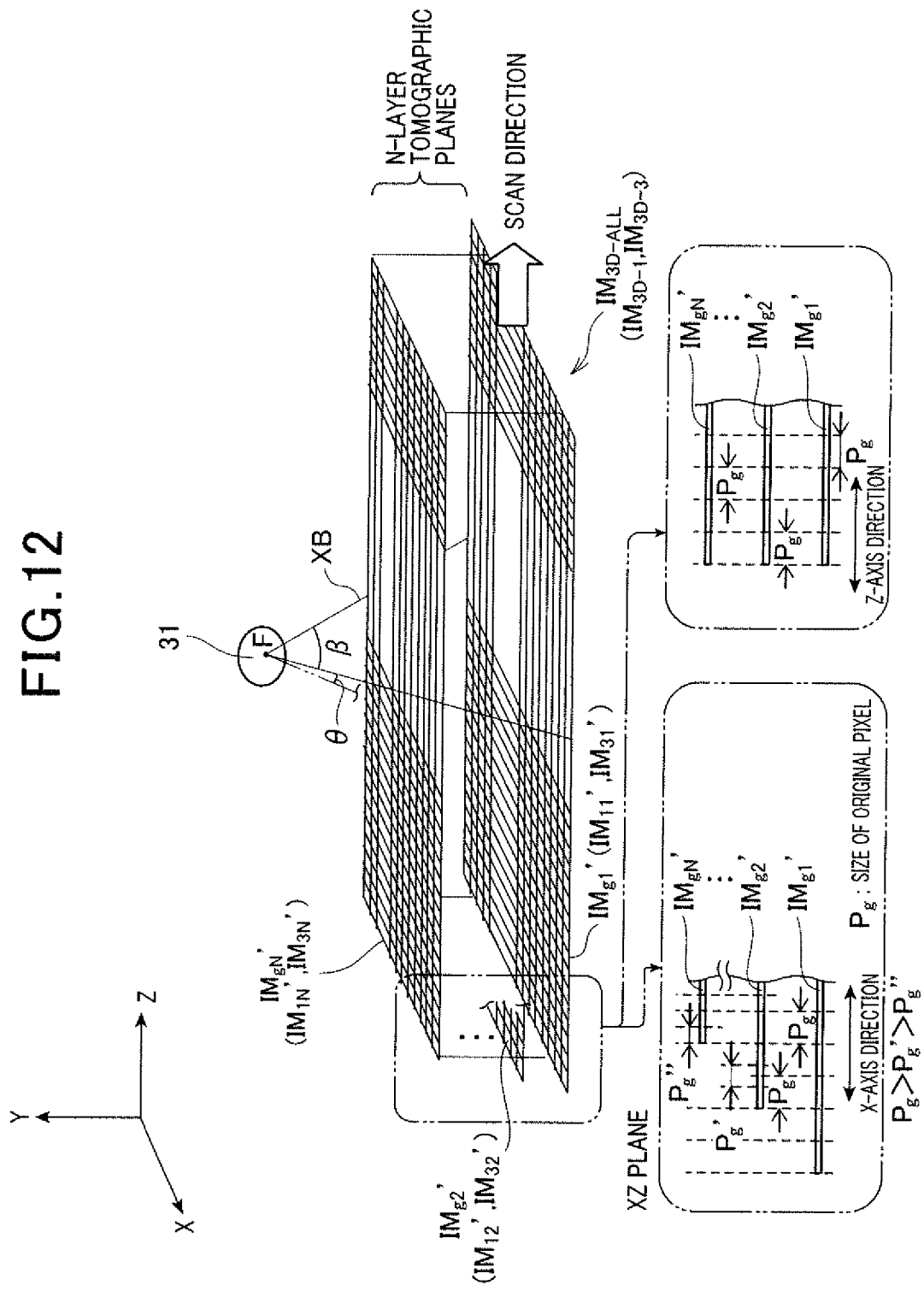
FIG. 12 is a diagram for explaining the data of a plurality of tomographic images that are virtually arranged in an inspection space.

The data of the rectangular area images IMg1', and IMg2' to IMgN' are three-dimensionally arranged in an object space (that is, the inspection space SP) that is virtually provided by the buffer. As a result, as schematically shown in FIG. 12, a three dimensional image IM3D-ALL composed of the two-dimensional rectangular area images IMg1' and IMg2' to IMgN' is formed. In FIG. 12, the images IMg1' and IMg2' to IMgN' are each shown in the form of a sheet that has no thickness.

In addition, the buffer for substance identification 60 performs a process similar to that described above on the reconfigured tomographic images IM11 to IM1N and IM31 to IM3N. That is, for these tomographic images, three-dimensional images IM3D-1 and IM3D-3 composed of the respective two-dimensional rectangular area images IM11' and IM12' to IM1N', and IM31' and IM32' to IM3N' for the first and third energy ranges are formed in a manner similar to that in the schematic drawing in FIG. 12.

In the data of the three dimensional image IM3D (IM3D-1 and IM3D-3) shown in FIG. 12, the sizes of the plurality of tomographic images IMg1', IMg2', IMg3', . . . IMgN' are such that the areas thereof (that is the size in the belt width direction X) decrease as the tomographic plane advances towards the upper side in the height direction Y. That is, the sizes of the plurality of tomographic images IMg1', IMg2', IMg3', . . . IMgN' become smaller in a pyramid-like manner (more accurately, a step-like manner) as a result of the scaling effect in the belt width direction X of the X-ray beam XB. Of the sizes of the plurality of tomographic images IMg1', IMg2', IMg3', . . . IMgN', the image size of the bottommost image tomographic image IMg1' is the original pixel size and is a square. However, the tomographic images IMg2', IMg3', . . . IMgN' positioned above the bottommost tomographic image IMg1' form increasingly narrow rectangles as the position of the tomographic plane advances to the upper side (Y axis direction). As a result, the number of pixels is the same in all of the tomographic images IMg1', IMg2', IMg3', . . . IMgN'. In addition, the positions on the XZ plane of the respective pixels positioned in the center of the image data coincide among the data of the tomographic images IMg1', IMg2', IMg3', . . . IMgN'.

Figure 13:
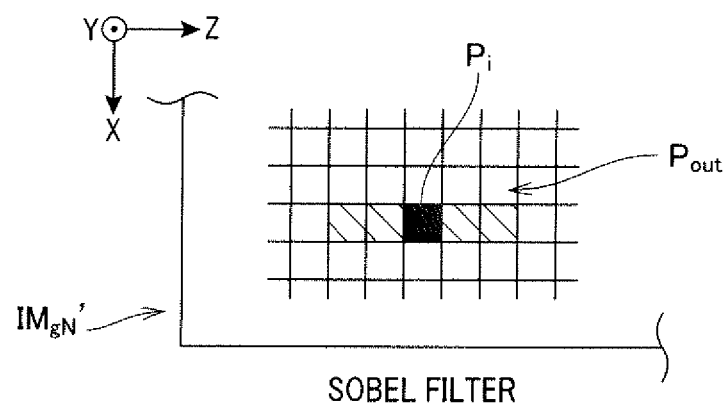
FIG. 13 is a diagram for explaining a Sobel filter process that serves as edge detection.
Figure 14:
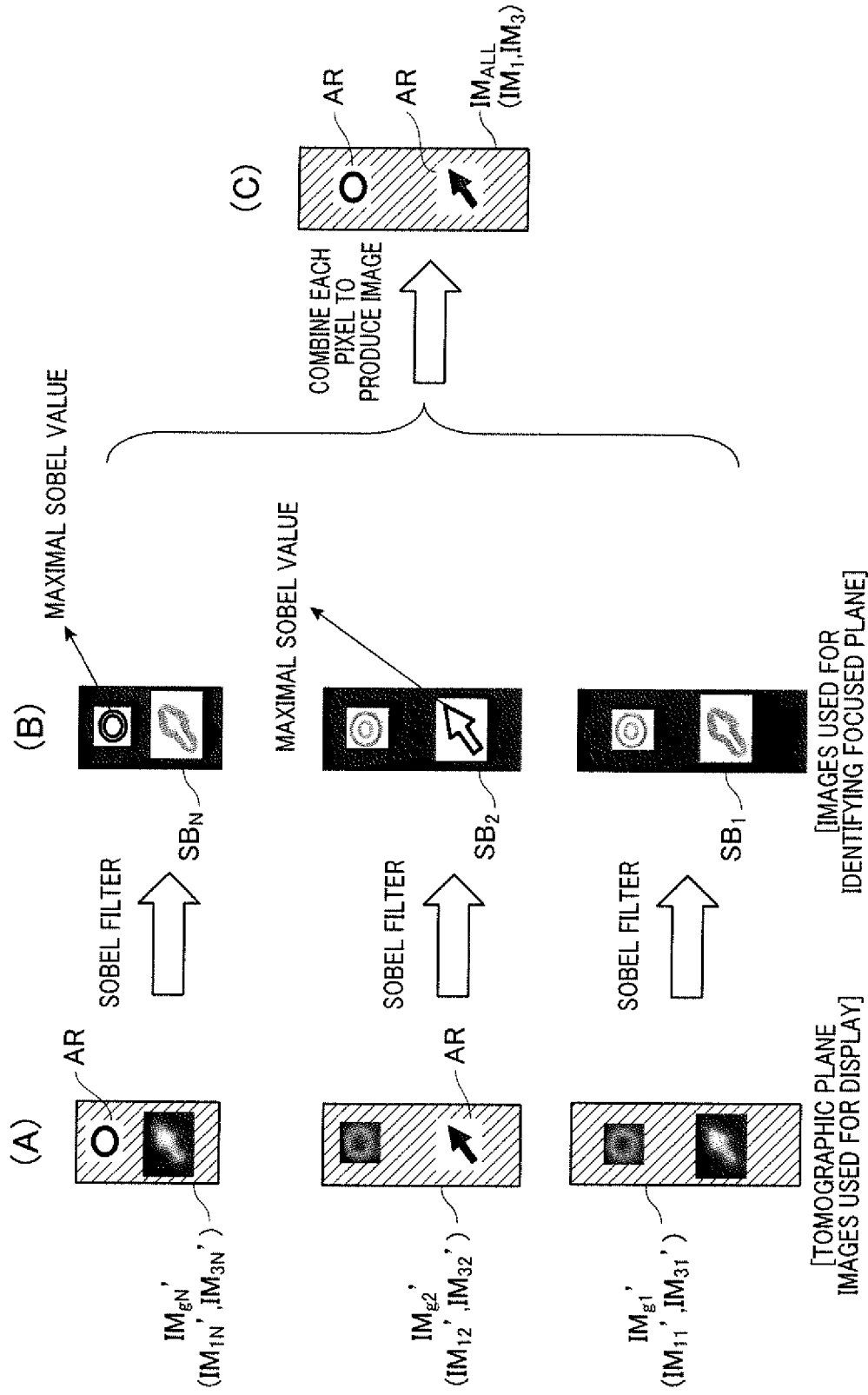
FIG. 14 is a diagram for explaining a process for generating a single composite image having an optimal focal point from a plurality of tomographic images and images thereof on which the Sobel filter has been applied.

Next, the edge detection circuit 61 reads out the data of the three-dimensional image IM3D from the buffer for display 59 and applies the Sobel filter on each pixel in each tomographic image. As schematically shown in FIG. 13, the Sobel filter calculates the primary spatial differentials of the values of a plurality of pixels Pout (slanted line portions) that are one-dimensionally arrayed with a pixel Pi at the center in the scan direction. Calculation is then performed on each pixel with the primary spatial differential value (Sobel value) as the edge information. As a result, the sections at which the pixel values change in each tomographic image, that is, the edge (contour) of the area of the object OB that appears in the tomographic image IMgN' can be detected.

The Sobel filter may be a two-dimensional filter or a combination of the Sobel filter and another filter. Furthermore, in the edge detection, the edge detection filter may be an edge detection filter other than the Sobel filter, such as a one-dimensional MAX-MIN filter or a Prewitt filter, or a combination of such filters and another filter.

The output from the edge detection circuit 61, that is, the Sobel values (the primary spatial differential values: edge information) are successively sent to the combining and editing circuit 62.

The combining and editing circuit 62 is configured to map the inputted Sobel value at the position of the pixel in each of the tomographic images IMg1', IMg2', IMg3', . . . IMgN' described above. The combining and editing circuit 62 thereby composites three-dimensional distribution data of the Sobel values in which a plurality of two-dimensional data groups are stacked. Specifically, a first circuit 62A of the combining and editing circuit 62 is configured to gen-erate two-dimensional images SB1, SB2, . . . , SBN of which the Sobel values shown in FIG. 14(B) are the pixel values, from the tomographic images IMg1', IMg2', IMg3', IMgN' shown in FIG. 14(A).

Furthermore, a second circuit 62B of the combining and editing circuit 62 is configured to virtually stack the two-dimensional images SB1, SB2, . . . , SBN and generate a three-dimensional distribution SB3D schematically shown in FIG. 15(A), in which the Sobel values are the pixel values. The data of the three-dimensional distribution SB3D is three-dimensionally stored in association with an address simulating the object space, within a memory space of the combining and editing circuit 62. The three-dimensional distribution SB3D of the Sobel values is outputted at a fixed cycle to the three-dimensional (3D) data output circuit 69.

Figure 15:
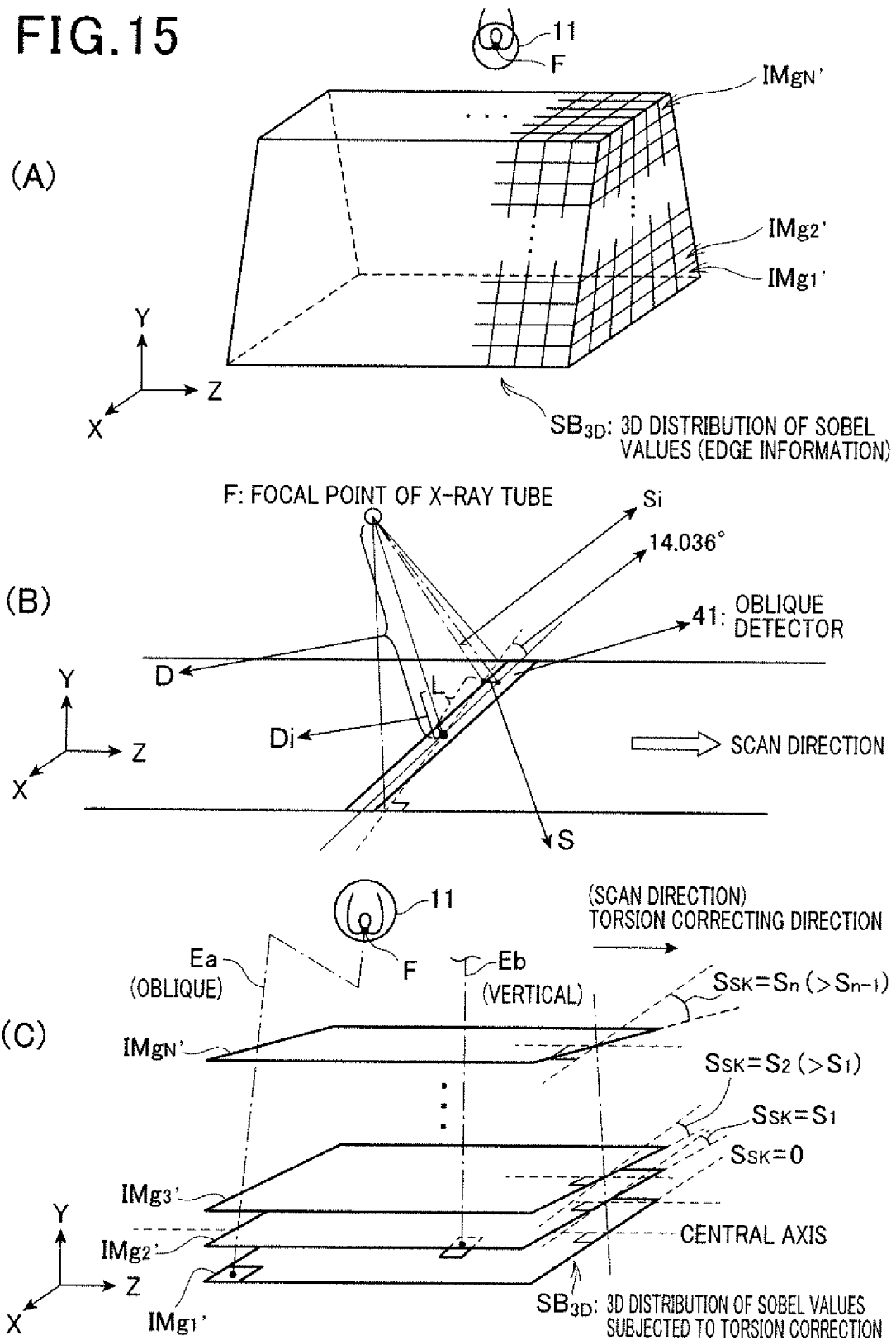
FIG. 15 is a diagram for explaining a three-dimensional distribution of Sobel values and a line of sight indicating a search direction for the Sobel values.

In the three dimensional distribution SB3D schematically shown in FIG. 15, in which the Sobel values are the pixel values, the size in the scan direction (Z-axis direction) of each pixel remains the same even when the position of the tomographic plane (position in the Y-axis direction) changes, in a manner similar to that described regarding FIG. 12. However, in the direction (X-axis direction) perpendicular to the scan direction, the size of each pixel decreases as the position of the tomographic plane becomes higher. As a result, the numbers of vertical and lateral pixels are set to be fixed for each tomographic plane.

Next, a unique correction process according to the present embodiment will be described with reference to FIGS. 15(B) and (C). According to the present embodiment, as shown in FIG. 3, the detector 41 is arranged such as to be tilted at the angle $\alpha°$ (such as $14.036±0.5°$) in relation to the scan direction. In addition, the X-rays from the tube focal point F that can be considered substantially a spot is radiated over the fan angle $\beta$.

The geometric arrangement relationship will be described based on the model in FIG. 15(B). In FIG. 15(B), D: the height between the X-ray tube and the detector;

Di: the height between the detector and a tomographic plane i;

L: the deviation distance between the center Od of the detector in the scan direction and the center of the reconfigured image;

S: the deviation direction from an orthogonal coordinate system resulting from the tilted arrangement of the detector, of the deviation distance L when the tomographic plane is at the position of the detector plane;

Si: the deviation distance from an orthogonal coordinate system resulting from the tilted arrangement of the detector, of the deviation distance L on a tomographic plane at height Di:

$$S = L \times \tan 14.036°; \text{ and}$$

$$Si = S \times (D - Di)/D.$$

As the foregoing indicates, no "torsion (or twist)" is present in the X-ray radiation at the center Od on the plane of the detector 41. However, the X-ray radiation is twisted at other positions. The amount of torsion (=S−Si) increases as the height Di of the tomographic plane increases. A reason for this is that, in the various processes described above, a process to perform calibration such that the torsion=0 at the tomographic plane corresponding to the plane of the detector is performed.

Here, a third circuit 62C of the combining and editing circuit 62 performs "torsion correction" to shift, by an amount equivalent to the amount of torsion S−Si, the pixel positioned at distance L on the tomographic plane at height Di, for each tomographic plane. That is, the combining and editing circuit 62 shifts the pixel in the three-dimensional distribution SB3D in which the Sobel values are the pixel values, generated as in FIG. 15A, by the above-described torsion correction amount (Ssk=S−Si) in the torsion correction direction (same as the scan direction), for each tomographic plane and for each pixel.

As a result, the three-dimensional distribution SB3D in which the Sobel values serve as the pixel values and on which torsion correction has been performed is generated as shown in FIG. 15(C). When FIG. 15(C) is viewed along the Y-axis direction, the tomographic image IMg1' of the bottommost layer corresponding to the position of the detector surface forms a rectangle along the XZ-plane orthogonal system (Z axis=center axis of the rectangle). However, as the schematic drawings of the tomographic images IMg2', IMg3', . . . IMgN' of the second layer, the third layer, . . . , the N-th layer indicate, the torsion correction amount SsK gradually increases from Ssk=0 (see Ssk=S1, S2, . . . Sn−1, Sn in FIG. 10(C)) as the tomographic plane becomes higher than the tomographic plane IMg1' in the Y axis direction. Therefore, when the tomographic images in the second and subsequent layers are viewed in the Y-axis direction, a parallelogram that is further tilted towards the scan direction as the position becomes higher is formed, and the squashing of the parallelogram increases towards the upper layers.

The combining and editing circuit 62 may be configured to perform the torsion correction at the same time the data of the three-dimensional distribution shown in FIG. 15(A) is generated. In addition, when the width of the scan range in the direction perpendicular to the scan is narrow, the torsion correction may be omitted. However, from the perspective of ensuring accuracy in blur correction, the torsion correction is preferably performed.

Furthermore, as shown in FIG. 15(C), a fourth circuit 62D of the combining and editing circuit 62 is configured to search the data of the three-dimensional distribution SB3D on which torsion correction has been performed, from the center position of each pixel in the tomographic image IMg1' of the bottommost layer corresponding to the surface of the detector 41 along the tilted direction towards the tube focal point F of the X-ray tube 31, as indicated by line of sight Ea, to retrieve for the maximum value (or the local maximum value) of the Sobel values present on this line of sight. At this time, the pixel size decreases (the size in the direction perpendicular to the scan direction decreases) as the line of sight Ea advances towards the tube focal point F. Therefore, because the Sobel values are required to be searched in the same pixel size, the same pixel size is ensured for the pixels in the tomographic planes above the surface of the detector (that is, the bottommost tomographic plane) by the subpixel method or the like, and edge search of the pixel values, that is, the Sobel values is performed. Because the line of sight Ea extends at an angle, all that is required in this search is that the maximum value (or the local maximum value) be determined by the same object being determined by only the difference in the degree of blurring, at the position of each tomographic plane. The search conducted on the Sobel values along the tilted line of sight matches the tilted radiation field having the fan angle β of the X-rays. Therefore, the accuracy of the search on the Sobel values increases.

The search on the Sobel values may be that in which the search is performed along a line of sight Eb that extends in the height direction Y (that is, vertically) from the center position of each pixel in the bottommost tomographic image IMg1' (see FIG. 15(C)), and the maximum value (or the local maximum value) of the Sobel values present on the line of sight Eb is retrieved.

Figure 16:
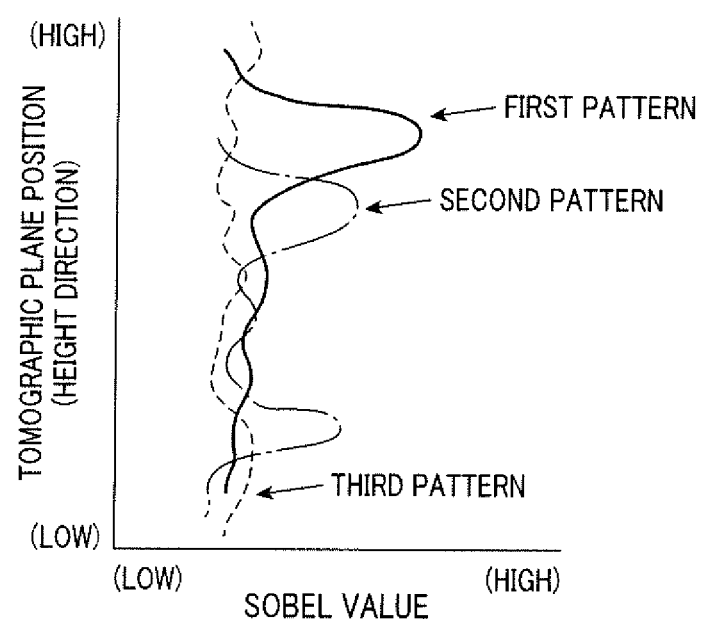
FIG. 16 is a graph showing an example of profiles in relation to tomographic plane positions of the Sobel values for each pixel and the pattern classification thereof.

As a result of the search, for example, as shown in FIG. 16, various profiles of the Sobel values are determined for each line of sight Ea (Eb), that is, for each pixel of the detector 41 in the object space. In the profiles in FIG. 16, the lateral axis is the Sobel value, and the vertical axis indicates the position in the height direction, that is, the position of the tomographic plane. The profile data is outputted to the edge information indexing circuit 70 at a fixed cycle.

Furthermore, a fifth circuit 62E of the combining and editing circuit 62 identifies the position in the height direction of the tomographic image, that is, the position of the tomographic plane having the maximum value (or the local maximum value) of the Sobel values for each pixel, as a result of the search on the Sobel values described above. In the identifying process, the position of the tomographic plane is preferably identified taking into consideration not only the maximum value (or the local maximum value) of the Sobel values but also the Sobel values of each pixel themselves and the variations thereof. The identification information is also outputted to the first image generating circuit 63, the second image generating circuit 65, and the edge information indexing circuit 70, at a fixed cycle.

The above-described edge information indexing circuit 70 sorts the inputted profile data into a plurality of types of patterns determined in advance for each pixel. In this example, a first pattern is a pattern in which a single Sobel value peak is present in the position of a certain pixel. A second pattern is a pattern in which a plurality of Sobel value peaks are present in the position of a certain pixel. A third pattern is a pattern in which a specific peak cannot be found in the changes in the Sobel value in the position of a certain pixel. For example, when foreign matter that may be present within the object OB is presumed, the first pattern indicates the likelihood of the pixel being that in which the foreign matter is present, for example. The second pattern indicates the likelihood of the pixel being that in which the foreign matter and the object to be inspected, or pieces of foreign matter, are projected in an overlapping manner. The third pattern indicates that the likelihood is high that there is no inclusion of foreign matter and no edge of the object to be inspected. In other words, the third pattern indicates a region that is not of interest.

Sorting into the foregoing patterns of the profile is performed by a curve obtained as a result of the search on the Sobel values in the tilted direction (or the vertical direction) being smoothed and a threshold process or the like being performed thereon.

Here, the edge information indexing circuit 70 expresses the sorted profile data by an index comprising two bits. For example, when the profile data belongs to the first pattern, bits "00" are assigned. When the profile data belongs to the second pattern, bit "01" are assigned. Furthermore, when the profile data belongs to the third pattern, bits "10" are assigned. The profile of the Sobel values for each pixel is thereby indexed. The assigned two-bit data indexed for each pixel is sent to the data selector 67 at a fixed cycle.

An object of the present embodiment is to reduce the amount of information sent to the computer 23 from the detecting, or in other words, achieve high speed detection. Therefore, a significantly higher speed can be achieved by the indexed data being sent, rather than the profile data of the Sobel values being outputted as is.

Meanwhile, in the first image generating circuit 63, for each pixel, information designating the tomographic image from which to acquire the pixel value configuring the pixel is inputted. Therefore, the first image generating circuit 63 generates a single composite planar image $IM_{ALL}$ based on the designation information and the image data of the above-described tomographic images IMg1', IMg2', IMg3', . . . IMgN'. The first image generating circuit 63 is also formed by an FPGA, in a manner similar to the other circuits.

Specifically, for each pixel designated by the designating information, the first image generating circuit 63 selects a pixel positionally corresponding to the designated pixel from the designated tomographic image among the plurality of tomographic images described above, and acquires the pixel value. This process is performed for all pixels. All of the pixels acquired in this way are combined into the single composite planar image $IM_{ALL}$.

The process, in more general terms, is as follows with reference to the example in FIG. 14(B). Among the Sobel values SB1, SB2, . . . , SBN, regarding the Sobel value in the upper frame, the pixel portion indicated by a circle has a local maximum value in the height direction Y, that is, edge information indicating a sudden change in luminance from the peripheral portion. Regarding the Sobel value in the middle frame, the pixel portion indicated by an arrow has a local maximum value in the height direction Y. Furthermore, the Sobel value in the lower frame has no local maximum value. A maximum value may be used instead of the local maximum value.

Here, the first image generating circuit 63 selects only the pixels in the plurality of tomographic images that have the Sobel value SB1 of the lower frame that is a square and has the maximum pixel size, and that positionally correspond to the pixels having the local maximum Sobel values along the line of sight Eb (or Ea), for each pixel. The first image generating circuit 63 thereby generates the single composite planar image (two-dimensional image) $IM_{ALL}$ shown in FIG. 14(C). That is, in the planar image $IM_{ALL}$, image portions (both the circle and the arrow) of the composite images IMg2 and IMgN that correspond to the pixels in which both Sobel values SBN and SB2 of the two frames indicate local maximum values appear. In other words, the composite planar image $IM_{ALL}$ is a two-dimensional image in which, when the object OB is radioscopically viewed at an angle (or vertically), downward from above in the height direction, a substance AR (that is, a substance that is highly likely to be foreign matter) present inside the target OB (food product) is projected in optimal focus on the XZ plane. The substance AR has an X-ray transmission rate that is relatively different from that of the medium of the overall target present within the object.

Figure 17:
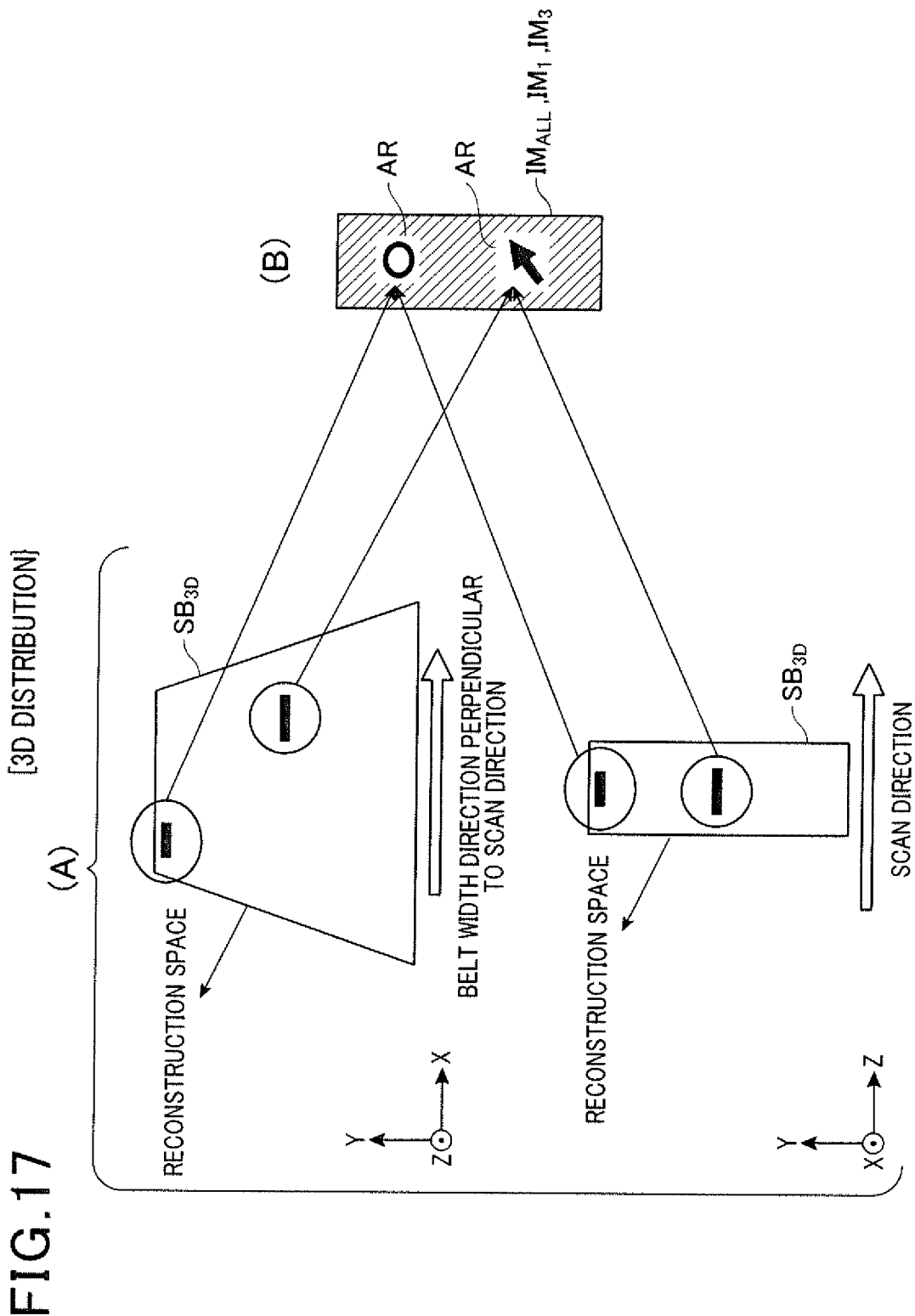
FIG. 17 is a diagram for explaining a positional relationship of foreign matter between a reconfiguration space formed by a plurality of tomographic images and a single composite image having an optimal focal point.

The planar image functions as a radioscopic image. Therefore, should even a single piece of foreign matter AR, or a plurality thereof, be three-dimensionally present inside the object OB, the planar image can be observed as a planar image in which the AR is projected. This aspect is shown in FIG. 17. In the example in FIG. 17(A), two pieces of foreign matter AR indicated by a circle and an arrow are present inside the three-dimensional object OB. However, although the two pieces of foreign matter AR differ from each other in both the position in the belt width direction X and the position in the scan direction Z, in the single planar image, all sections are visualized in optimal focus. That is, the composite planar image $IM_{ALL}$ is an image in which all pixels are in optimal focus, and is an image that can also be said to be an all-pixel-in-focus image.

The data of the composite planar image $IM_{ALL}$ that has been generated as described above is subjected to a de-noising process by the first de-noising circuit 64 in the next stage. The data of the composite planar image $IM_{ALL}$ is then sent to the computer 23 via the data selector 67 and the image output port 68, at a fixed cycle.

Meanwhile, the three-dimensional Sobel value IM3D that has been sent to the three-dimensional data output circuit 69 is also sent to the computer 23 via the data selector 67 and the image output port 68.

Depending on the setting state of the data selector 67, any one, two, or all of the data of the composite image $IM_{ALL}$, the indexed data of the Sobel values, and the three-dimensional Sobel value IM3D can be sent to the computer 23 via the image output port 68.

The computer 23 displays the composite planar image $IM_{ALL}$ and the three-dimensional image IM3D in an appropriate aspect on the display 23B thereof. The computer 23 thereby visually provides the operator with image information for foreign matter determination. For example, when the presence of foreign matter is discovered through appropriate processing, the computer 23 may perform a process (corresponding to a notifying means) to give notification of the presence of foreign matter through the display 23B.

In addition, the data of the composite planar image $IM_{ALL}$ and the three-dimensional image IM3D is stored and held in the memory 23M (storage means) of the computer 23. Therefore, the operator can read out the image data at any time and can carefully observe the area of interest by performing appropriate post-processing. For example, the operator can perform processes such as enlarging, and displaying in detail, only a specific area by setting an ROI in the three-dimensional Sobel value $IM_{3D}$, or observing the overlap between pieces of foreign matter, or a piece of foreign matter and the edge of the object to be inspected, by designating a specific tomographic plane (Sobel value) in the height direction.

Meanwhile, to perform substance identification on the object OB, as described above, the buffer for substance identification 60 receives the tomographic image data IM related to the first and third energy range frame data $FD_1"$ and $FD_3"$ from the logarithmic conversion circuit 58. Therefore, the buffer 60 provides the second image generation circuit 65 with the tomographic image data IM upon converting the tomographic image data IM to an appropriate format.

Here, the second image generation circuit 65 generates each of the first and third energy range in-focus planar images IM1 and IM3, each of which is a single in-focus planar image. That is, the second image generation circuit 65 is provided with position information on the in-focus cross-section for each pixel from the combining and editing circuit 62. Therefore, based on the position information, the second image generation circuit 65 selects, for each pixel, the in-focus pixel from the reconfigured three-dimensional images based on the first and third energy range frame data $FD_1$ and $FD_3$ provided by the buffer for substance identification 60, and generates each of the first and third energy range composite planar images IM1 and IM3. The first and third energy range composite planar images IM1 and IM3 differ from the composite planar image $IM_{ALL}$ that is generated from the overall energy ranges, in that the base frame data $FD_1$ and $FD_3$ used to generate the composite planar images IM1 and IM3 are collected from the first and third energy ranges Bin1 and Bin3. Therefore, the first and third energy range composite planar images 1M1 and IM3 are schematically expressed in a manner similar to that in FIG. 14(C), described above.

In this way, according to the present embodiment, the first and third energy range composite planar images IM1 and IM3 are also planar images composed of three-dimensionally positioned pixels, in the same manner as the composite planar image $IM_{ALL}$ that is generated from the overall energy ranges. The first and third energy range composite planar images IM1 and IM3 can be considered representative images representing the object to be inspected OB that are used for substance identification.

In addition, the second image generation circuit 65 is provided with imaging mode information from the computer 23. The imaging mode information indicates "foreign matter detection, substance identification, or both". Therefore, the second image generation circuit 65 may generate (or prepare) a selective image based on either of foreign matter detection and substance identification, or both.

The first and third energy range composite planar images IM1 and IM3 generated (or prepared) by the second image generation circuit 65 is subjected to a predetermined de-noising process by the second de-noise circuit. Thereafter, in a manner similar to that described above, the first and third energy range composite planar images IM1 and IM3 are sent to the computer 23 via the data selector 67 and the image output port 68.

Therefore, the computer 23 can also visually provide the first and third energy range composite planar images IM1 and IM3 for foreign matter determination through the display 23B, in a manner similar that described above. In addition, the computer 23 can also perform a process for identifying the type and/or properties of a single or a plurality of substances forming the object OB based on a predetermined algorithm, together with, or separately from, provision of the image information for foreign matter determination. The scheme for substance identification is known by, for example, JP-A-2013-119000.

In the circuit configuration in FIG. 6, described above, the circuit elements 51 to 56 configure a frame data generating means. The reconfiguration circuit 57 corresponds to the tomographic image generating means. Of the circuit elements 51 to 56, the image reduction circuit 56 also functions as a tomographic plane data generating means and a positioning means.

In addition, the circuit elements 58 to 61 and a portion of the circuit element 62 configure the edge information generating means. Furthermore, a portion of the circuit element 62 and the circuit element 63 configure the composite image generating means. Moreover, the circuit elements 64, 67, and 68 form an edge information output means.

In addition, the buffer for display 59 also functions as an editing means and a clipping means. Furthermore, the edge information indexing circuit 70 functions as an edge information indexing means, as well as a patterning means, an index calculating means, and an index output means. In addition, the computer 23 functionally functions as a composite image providing means, a designating means, and the notifying means.

In this way, in the X-ray inspection apparatus 20 according to the present embodiment, a plurality of tomographic images within a range designated in the height direction in the object space, that is, the inspection space SP in which the object is placed, is generated from the X-ray transmission data detected by the X-ray detector 41. The plurality of tomographic images are generated taking into consideration the spreading in the inspection space of the X-rays radiated from the X-ray tube 31 and the differences in height from the detection surface of the X-ray detector 42. From each of the plurality of tomographic images, that is, from the object space, the edge information resulting from the presence of a substance such as foreign matter is extracted in a three-dimensional manner. Based on the extracted information, the single composite planar image $IM_{ALL}$ in which the pixels in the tomographic images are optionally selected regardless of the tomographic plane position and combined is generated. The composite image $IM_{ALL}$ shows an aggregation of sections that are in optimal focus in each tomographic image. Therefore, the foreign matter inside the object is also favorably visualized. As a result, the foreign matter (a substance differing in composition from that of the object) present inside the object can be visualized at a higher resolution, and the presence of the foreign matter can be more easily detected with higher reliability.

Furthermore, according to the present embodiment, the three-dimensional Sobel value IM3D is also outputted from the X-ray detecting unit 22, or specifically, the data processing circuit 42 that is an element on the detection side. Therefore, the three-dimensional Sobel value IM3D can be used by post processing as auxiliary display data for foreign matter detection or, in some cases, the main processing data. For example, usage such as checking a region of interest in the composite planar image $IM_{ALL}$, described above, using the three-dimensional Sobel value IM3D becomes possible.

In addition, according to the present embodiment, when the X-ray detecting unit 22 passes the detection data to the computer 23, an image required for foreign matter detection, that is, the composite planar image $IM_{ALL}$, the three-dimensional Sobel value $IM_{3D}$, and/or the indexed data of the Sobel values (data indicating the pattern type) are already generated on the detecting unit side. That is, only data that has already been pre-processed is transmitted at a fixed interval to the computer 23. Therefore, although delay amounting to a pipeline process by the data processing circuit (such as a hardware circuit configured by an FPGA) occurs, data on which the above-described various processes have been performed is outputted from the detector 41 at high speed at a fixed interval. Therefore, even when the detector 41 detects frame data at a high speed rate, the amount of data transfer from the X-ray detecting unit 22 to the computer 23 can be reduced and a higher-speed detection operation by the detector 41 becomes possible.

Third Embodiment

Next, an X-ray inspection apparatus according to a third embodiment that is a further expansion of the above-described X-ray inspection apparatus 20 according to the second embodiment will be described with reference to FIG. 18 to FIG. 21. According to the present embodiment, constituent elements that are the same as or equivalent to those according to the second embodiment are given the same reference numbers. Descriptions thereof are omitted or simplified.

Figure 18:
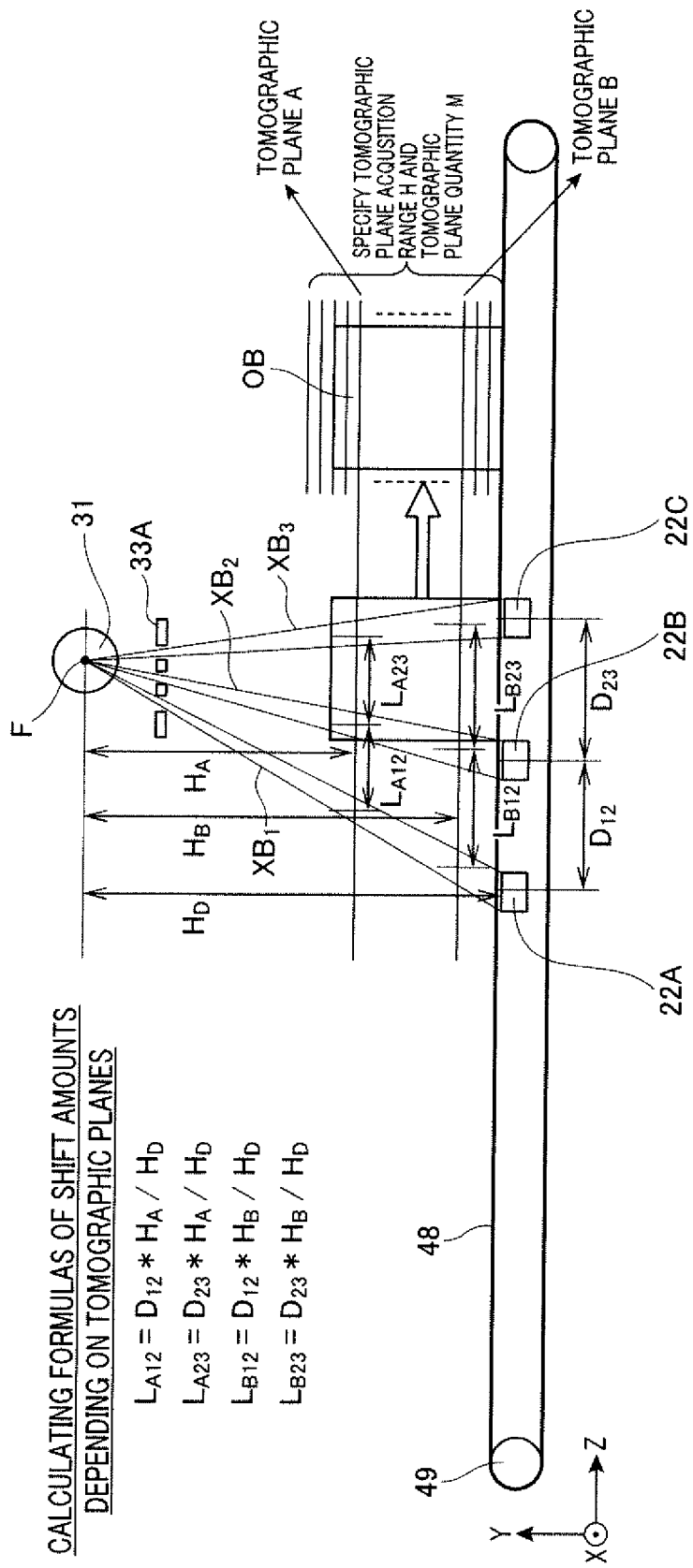
FIG. 18 is a configuration diagram for explaining the concept behind the configuration of an X-ray inspection apparatus according to a third embodiment of the present invention.
Figure 19:
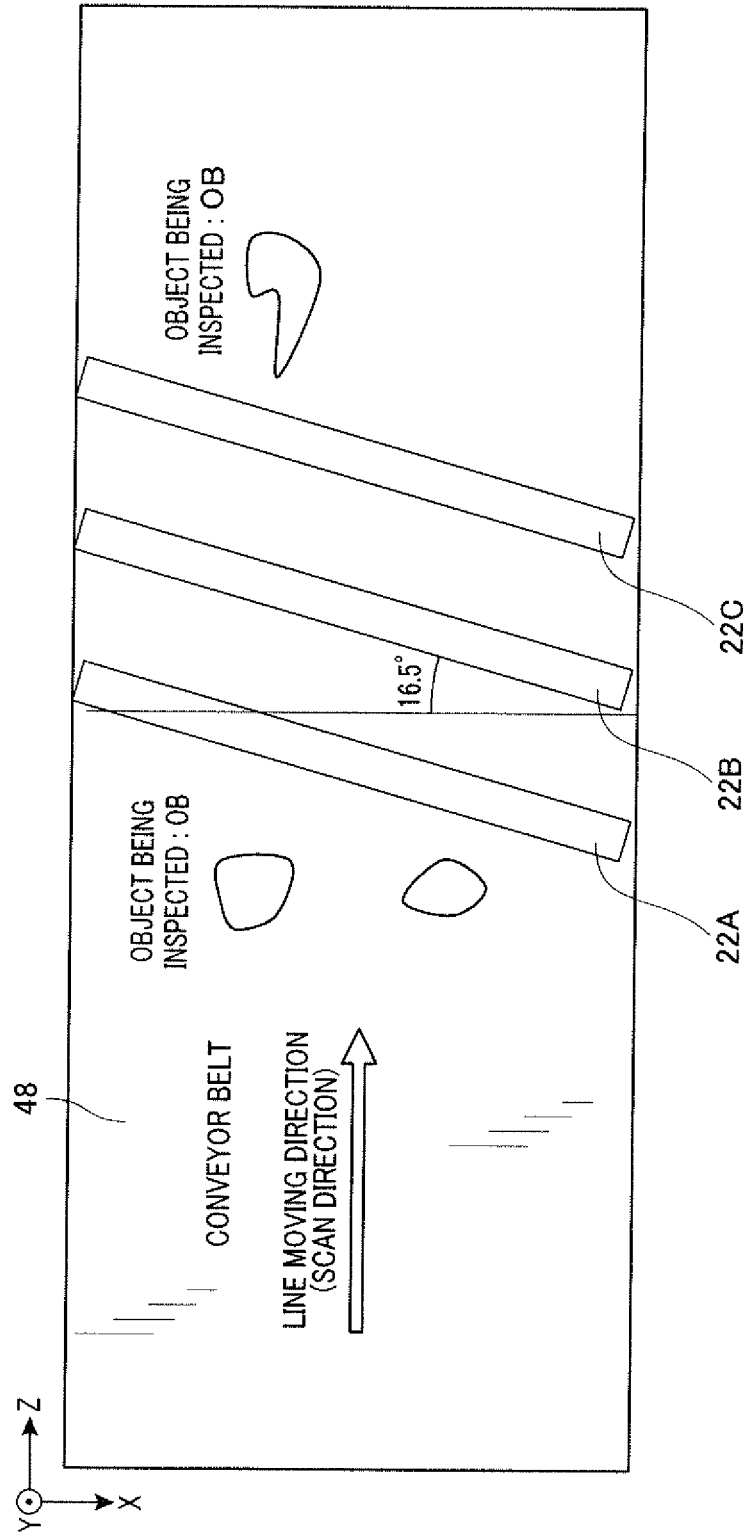
FIG. 19 is a diagram for explaining an example in which a plurality of detectors are arranged at an angle according to the third embodiment.

An X-ray inspection apparatus 80 includes the single X-ray tube 31, described above, and three X-ray detecting units 22A, 22B, and 22C that are arranged in a dispersed manner along the conveyor belt 48, that is, the scan direction Z. Each of the three X-ray detecting units 22A, 22B, and 22C is integrally provided with the X-ray detector 41 and the data processing circuit 42, in a manner similar to that described above. As shown in FIG. 18 and FIG. 19, the X-ray detecting units 22A, 22B, and 22C are each arranged such as to be tilted at an angle of substantially 14.036±0.5° in relation to the belt width direction X and parallel to each other.

The X-rays radiated from the X-ray tube 31 are generated as three X-ray beams XB1, XB2, and XB3 by a collimator 33A (forming a beam dividing means) that has three openings. The contours of the three X-ray beams accurately match the edges of the X-ray incidence windows of the three X-ray detectors 41 that are irradiated in a dispersed manner along the scan direction Z.

As shown in FIG. 18 and FIG. 19, here, the intervals between the center positions in the scan direction Z of the three X-ray detecting units 22A, 22B, and 33C (that is, the X-ray detectors 41) are D12 and D23. The intervals between the beam center positions at the height of a tomographic plane A are LA12 and LA23. The intervals between the beam center positions at the height of a tomographic plane B (lower than the tomographic plane A) are LB12 and LB23. Furthermore, the height between the X-ray tube focal point F and the conveyor belt 48 is HD. The heights between the tomographic planes A and B, and the X-ray tube focal point F are HA and HB. Still further, the amounts of shifting LB12 and LB23 when the reconfigured images at the height of the tomographic plane B are added together are expressed as follows:

$$LB12 = D12 \times HB/HD$$

$$LB23 = D23 \times HB/HD$$

In a similar manner, the amounts of shifting LA12 and LA23 when the reconfigured images at the height of the tomographic plane A are added together are expressed as follows:

$$LA12 = D12 \times HA/HD$$

$$LA23 = D23 \times HA/HD$$

Therefore, in each of the three X-ray detecting units 22A, 22B, and 22C, the frame data that is detected in a manner similar to that according to the second embodiment is reconfigured for each detection system. The pieces of frame data are then added to each other based on the amount of shifting exemplified by the above-described amounts of shifting LA12, LA23, LB12, and LB23. An aspect of this addition is schematically shown in FIGS. 20(A) and (B). In the case of this example, because the tomographic plane A is positioned above the tomographic plane B, the amount of shifting for addition is smaller by the same extent.

Figure 21:
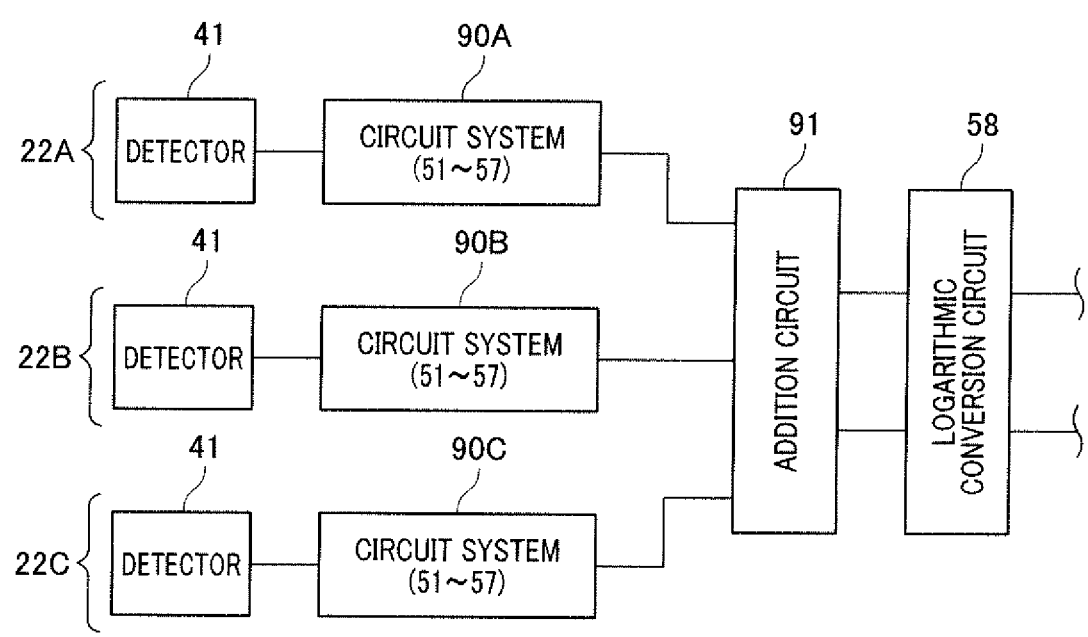
FIG. 21 is a simple, partial block diagram for explaining image addition according to the third embodiment.

In a configuration such as this in which a plurality of X-ray detecting units, such as three X-ray detecting units 22A, 22B, and 22C, that is, three X-ray detectors 41 are arranged in a dispersed manner, the data processing circuit 42 shown in FIG. 6 requires a circuit for performing the addition. In the configuration in FIG. 6, a circuit system from the signal collecting circuit 51 to the reconfiguration circuit 57 is independently required in correspondence to each of the three detectors 41. Therefore, between the three reconfiguration circuits 57 of the three circuit systems 90A to 90C and the single logarithmic conversion circuit 58, an addition circuit 91 may be provided. The addition circuit 91 adds the three reconfigured images based on the above-described amount of shifting for each height of the tomographic planes, for each pixel. This is shown in FIG. 21. Other circuit configurations are similar to those shown in FIG. 6.

In this way, according to the present configuration, as a result of the plurality of X-ray detectors being arranged such as to be dispersed in the scan direction, compared to when the X-ray detectors are not arranged in a dispersed manner and the radiation field is simply widened, wide-angle X-ray imaging can be performed while reducing the amount of X-rays that are irradiated onto the object OB. Therefore, even when the object is thick, or in other words, the height above the conveyor belt is high, the overall area of the object can be covered. At the same time, tomographic images exhibiting the tomographic effect can be obtained and high-resolution Sobel values can be obtained. In addition, the various working effects achieved according to the second embodiment can also be achieved.

The present invention is not necessarily limited to the configurations according to the above-described embodiments. The present invention may be carried out such as to be further expanded to various embodiments.

According to the above-described embodiments, an example is described in which the direction (trajectory) in which the object OB moves, that is, the scan direction Z is a straight line. However, when the detector and X-ray tube pair is moved, the direction (trajectory) is not necessarily required to be a straight line, and may be a curved line. When the scan direction is a curved line, the surface to be scanned is a curved surface. FIG. 22 shows an example of such a scan direction (trajectory) that forms a curved line. In the example in FIG. 22(A), a conveying means 95, such as a belt, that conveys the object to be inspected OB curves along a certain plane. The scan direction Z1 thereof forms a curved line between the X-ray tube 31 and the X-ray detecting unit 22. In addition, in the example in FIG. 22(B), the conveying means 95 curves in a three-dimensional space and similarly forms a three-dimensional curved line Z2. In such cases as well, all that is required is that the generated tomographic images be generated along the curved plane that is parallel to the belt surface. As a result, the present invention can also be achieved as a dental panoramic imaging apparatus for medical use or a non-destructive X-ray inspection apparatus on a curved path that curves on a belt conveyor that conveys items.

In addition, according to the above-described embodiments, when the first image generation circuit 63 composites the composite image on the single plane shown in FIG. 14(C), the first image generation circuit 63 selects and combines pixels from the plurality of tomographic images that have been reconfigured up to this point. However, the tomographic images subjected to pixel selection and combining are not limited to images of the tomographic planes that have been designated in advance in this way, that is, tomographic planes that already exist. For example, the tomographic plane may be positioned between two tomographic planes that are adjacent to each other, among the tomographic planes that have been designated in advance. The tomographic plane that is positioned therebetween in this way can be generated by an interpolation process from the two tomographic images on both sides thereof or tomographic images thereabove, based on the position. Therefore, a circuit that determines whether or not the tomographic plane position corresponding to the maximum value (or the local maximum value) designated based on the profile of the Sobel values in the height direction (vertical direction) in the object space corresponds to the position of an already existing tomographic plane, and the above-described correction circuit may be additionally mounted on the circuit configuration in FIG. 6. As a result, high spatial resolution can be maintained even when the number of tomographic planes that are designated in advance is small. Therefore, the amount of calculation required for the reconfiguration process by shift-and-add can be reduced.

According to the above-described embodiments, when only the composite image on a single plane shown in FIG.

14(C) is to be obtained, for simplicity, a maximum intensity projection (MIP) processing circuit may be used instead of the edge detection circuit 61, the combining and editing circuit 62, and the first image generation circuit 63.

REFERENCE SIGNS LIST 10, 20, 80 X-ray inspection apparatus
12, 21 X-ray generator
11, 31 X-ray tube
18, 22 X-ray detecting unit
13, 41 X-ray detector
14 frame data generating unit
15 tomographic image generating unit
16 edge information generating unit
16A edge information output unit
16B edge information indexing unit
17 composite image generating unit
17A composite image presenting unit
22 data processing circuit (LSI circuit)
23 computer
33, 33A collimator
42 data processing circuit
51 to 70 circuit elements included in data processing circuit
OB object to be inspected

The invention claimed is:

1. An X-ray inspection apparatus, comprising:
an X-ray generator provided with an X-ray tube having a point-shaped tube focal spot, the X-ray tube generating an X-ray beam from the tube focal spot, the X-ray beam having a given cone angle in a scan direction and a predetermined fan angle in a direction which is along a section perpendicular to the scan direction;
an X-ray detector provided with a plurality of pixels two-dimensionally arrayed and configured to output at a predetermined frame rate frame data presenting strength of the X-ray beam incident on the pixels, the X-ray detector having a detection surface, the pixels providing a rectangular shape as a whole thereof in the detection surface and being arranged to be oblique to the scan direction as a whole of the rectangular shape;
a moving member moving either a pair of the X-ray tube and the X-ray detector or the object relatively to the other,
the X-ray detector being arranged to be opposed and separated to and from the X-ray tube with a space provided therebetween, an object being inspected being positioned in the space, wherein either the pair of the X-ray tube and the X-ray detector or the object is moved such that a center line of the X-ray beam in a width direction thereof crosses with each of a plurality of tomographic planes virtually set in the space and parallel to the scan direction, a crossing length in each of the tomographic planes being always constant;
data acquiring circuitry acquiring the frame data outputted from the X-ray detector, while the moving member moves the pair of the X-ray tube and the X-ray detector or the object relatively to the other;
frame data generating circuitry generating, based on the frame data, frame data of each of the plurality of tomographic planes depending on a spread of the fan-shaped X-ray beam and positional differences of the plurality of tomographic planes in a perpendicular direction to the tomographic planes;
tomographic image generating circuitry for generating tomographic images of the tomographic planes by applying a laminography method to the frame data of the tomographic planes, generated by the frame data generating circuitry;
edge information generating circuitry generating a three-dimensional distribution of edge information based on calculating, every pixel of each of the tomographic images, edge information showing changes in pixel values of the respective tomographic images generated by the tomographic image generating circuitry;
correcting circuitry correcting, at each of the tomographic planes, the edge information in accordance with a difference in distances, the distances i) being taken between a center position, in the scan direction, of the rectangular shape provided by arrangement of the plurality of pixels and a position of each of the plurality of pixels and ii) depending on a height position in a radiation direction of the X-ray beam; and
composite image generating circuitry generating a single composite image through searching every pixel a three-dimensional distribution of the torsion-corrected edge information in a direction passing through the tomographic planes to detect a pixel showing a maximum of the edge information, selecting, at a pixel position corresponding to the detected pixel, only pixels of the tomographic images or other tomographic images generated from the tomographic images, and combining the selected pixels, the single composite image showing an inside state of the object.

2. The X-ray inspection apparatus of claim 1, wherein the direction passing through the tomographic planes is either a direction oriented from each of the pixels of the detector to the focal spot or a direction oriented upward from each of the pixels of the detector perpendicularly to a face of the pixels of the detector.

3. The X-ray inspection apparatus of claim 1, wherein the apparatus comprises composite image presenting circuitry visualizing and presenting the single composite image generated by the composite image generating circuitry.

4. The X-ray inspection apparatus of claim 3, wherein the apparatus comprises edge information output circuitry outputting data indicating the three-dimensional distribution of the edge information.

5. The X-ray inspection apparatus of claim 1, wherein the apparatus comprises specification circuitry specifying a range of the perpendicular direction, the range being occupied by the plurality of tomographic images,
wherein the specification circuitry is configured to specify the range as both thicknesses and a quantity of the tomographic planes.

6. The X-ray inspection apparatus of claim 1, wherein the frame data generating circuitry comprises tomographic-plane data generating circuitry configured to
i) reducing sizes of the pixels of the frame data at a same scale in both the scan direction and a direction perpendicular to the scan direction, by multiplying the respective the sizes of the pixels by a factor reflecting the positional difference of the tomographic planes in the perpendicular direction and
ii) generate, every tomographic plane, frame data generated by replacing the respective pixels of the frame data of the tomographic planes with pixels whose sizes in only the scan direction are in accordance with a same and desired resolution.

7. The X-ray inspection apparatus of claim 1, wherein tomographic image generating is configured to respectively reconstruct the tomographic images by applying a reconstruction process to the frame data of each of the plurality of tomographic planes generated by the tomographic-plane data generating circuitry, the reconstructed tomographic images having sizes of the frame data generated by the tomographic-plane data generating circuitry, the reconstruction process being based on the laminography method.

8. The X-ray inspection apparatus of claim 6, wherein the factors are defined by $$W_O = W \times (H_O/H_D),$$

wherein the X-ray detector has original pixels having a width W in the scan direction, the X-ray detector is distanced from the tube focal point of the X-ray tube by $H_D$, each of the plurality of tomographic planes is positioned $H_O$, and the tomographic image of each of the plurality of tomographic planes has the pixels having a width $W_O$ in the scan direction.

9. The X-ray inspection apparatus of claim 7, wherein
the reconstruction process is a shift & add process performed with the frame data, based on shift amounts which are set depending on a speed of the relative movement in the scan direction.

10. The X-ray inspection apparatus of claim 1, wherein the edge information generating circuitry comprises a configuration of applying an edge enhancement process to the plurality of tomographic images to calculate the edge information.

11. The X-ray inspection apparatus of claim 1, wherein
the X-ray detector has, at least, the two-dimensionally arrayed plural pixels of the X-ray detector are arranged obliquely to the scan direction, and
the frame data generating circuitry comprises
orthogonal-axis converting circuitry converting a direction of each of the pixels of the frame data outputted from the X-ray detector, into a group of pixels in an orthogonal axis system of which one axis is along the scan direction with the oblique arrangement still maintained.

12. The X-ray inspection apparatus of claim 11, wherein the oblique arrangement has an angle of 14.036±2.5 degrees.

13. The X-ray inspection apparatus of claim 1, wherein
the apparatus comprises beam splitting circuitry which splits the X-ray beam generated by the X-ray generator, into a plurality of X-ray beams in the scan direction;
the X-ray detector is composed of a plurality of X-ray detectors arranged discretely in the scan direction;
both the frame data generating circuitry and the tomographic image generating circuitry means are paired and a plurality of the pair are provided parallel to each other for each of the plurality of X-ray detectors; and
the apparatus comprises combined tomographic-image generating circuitry generating a single combined tomographic image through mutually combination of the plurality of tomographic images generated by each of the plurality of tomographic image generating circuitries, every position at each of which the tomographic image is set in the orthogonal direction, wherein the combined tomographic image generated by the combined tomographic-image generating circuitries is provided to the edge information generating circuitries as each of the plurality of tomographic images.

14. The X-ray inspection apparatus of claim 1, wherein the X-ray detector is a photon counting detector counting photons of the X-ray beam.

15. An inspection method performed by an X-ray inspection apparatus, the apparatus comprising:
an X-ray generator provided with an X-ray detector having a point-shaped tube focal spot, the X-ray detector generating an X-ray beam from the tube focal spot, the X-ray beam having a given cone angle in a scan direction and a predetermined fan angle in a direction which is along a section perpendicular to the scan direction; and
an X-ray detector provided with a plurality of pixels two-dimensionally arrayed and configured to output at a predetermined frame rate frame data presenting strength of the X-ray beam incident on the pixels, the X-ray detector having a detection surface, the pixels providing a rectangular shape as a whole thereof in the detection surface and being arranged to be oblique to the scan direction as a whole of the rectangular shape, the X-ray detector being arranged to be opposed and separated to and from the X-ray tube with a space provided therebetween, an object being inspected being positioned in the space,
wherein the method comprising steps of:
either a pair of the X-ray tube and the X-ray detector or the object is moved relatively to the other in the scan direction, the X-ray detector being arranged to be opposed and separated to and from the X-ray tube with a space provided therebetween, an object being inspected being positioned in the space, wherein either the pair of the X-ray tube and the X-ray detector or the object is moved such that a center line of the X-ray beam in a width direction thereof crosses with each of a plurality of tomographic planes virtually set in the space and
parallel to the scan direction, a crossing length in each of the tomographic planes being always constant, the frame data outputted from the X-ray detector being acquired while either the pair of the X-ray tube and the X-ray detector or the object is moved relatively to the other;
generating, based on the frame data, frame data of each of a plurality of tomographic planes depending on a spread of the fan-shaped X-ray beam and positional differences of the plurality of tomographic planes in a perpendicular direction to the tomographic planes, the tomographic planes being set in the space and parallel to the scan direction;
generating tomographic images of the tomographic planes by applying a laminography method to the generated frame data of the tomographic planes;
generating a three-dimensional distribution of edge information based on calculating, every pixel of each of the tomographic images, edge information showing changes in pixel values of the respective tomographic images generated;
correcting, at each of the tomographic planes, the edge information in accordance with a difference in distances, the distances i) being taken between a center position, in the scan direction, of the rectangular shape provided by arrangement of the plurality of pixels and a position of each of the plurality of pixels and ii) depending on a height position in a radiation direction of the X-ray beam; and
generating a single composite image through searching every pixel a three-dimensional distribution of the torsion-corrected edge information in a direction passing through the tomographic planes to detect a pixel showing a maximum of the edge information, selecting, at a pixel position corresponding to the detected pixel, only pixels of the tomographic images or other tomographic images generated from the tomographic images, and combining the selected pixels, the single composite image showing an inside state of the object.

* * * * *